United States Patent [19]

Snell

[11] Patent Number: 5,292,341
[45] Date of Patent: Mar. 8, 1994

[54] METHOD AND SYSTEM FOR DETERMINING AND AUTOMATICALLY ADJUSTING THE SENSOR PARAMETERS OF A RATE-RESPONSIVE PACEMAKER

[75] Inventor: Jeffery D. Snell, Northridge, Calif.

[73] Assignee: Siemens Pacesetter, Inc., Sylmar, Calif.

[21] Appl. No.: 844,818

[22] Filed: Mar. 2, 1992

[51] Int. Cl.⁵ ............................................ A61N 1/362
[52] U.S. Cl. ..................................................... 607/30
[58] Field of Search .................. 128/419 PG, 419 PT; 607/30

[56] References Cited

U.S. PATENT DOCUMENTS

| | | | |
|---|---|---|---|
| 4,513,743 | 4/1985 | van Arragon et al. | 128/419 PG |
| 4,712,555 | 12/1987 | Thornander et al. | 128/419 PG |
| 4,809,697 | 3/1989 | Causey III et al. | 128/419 PT |
| 4,825,869 | 5/1989 | Sasmor et al. | 128/419 PT |
| 4,940,052 | 7/1990 | Mann et al. | 128/419 PG |
| 4,940,053 | 7/1990 | Mann et al. | 128/419 PG |
| 4,979,507 | 12/1990 | Heinz et al. | 128/419 PG |
| 4,989,602 | 2/1991 | Sholder et al. | 128/419 D |
| 5,040,534 | 8/1991 | Mann et al. | 128/419 PG |
| 5,040,535 | 8/1991 | Mann et al. | 128/419 PG |
| 5,074,302 | 12/1991 | Poore et al. | 128/419 PG |

*Primary Examiner*—William E. Kamm
*Attorney, Agent, or Firm*—Bryant R. Gold; Leslie S. Miller

[57] ABSTRACT

A rate-responsive pacing system and method allows the inter-related sensor operating parameters associated with the physiological sensor of a rate-responsive pacemaker to be automatically and/or optimally set for a particular patient. The system includes both a pacemaker and an external programming device. The pacemaker includes appropriate memory circuits for recording a sensor indicated rate (SIR) signal in a histogram. The external programming device retrieves the SIR histogram data, as well as other data associated with the operation of the pacemaker, and selectively processes and displays such data in a prescribed manner. An Auto-Set sequence or routine, carried out by the external programming device, sets all of the rate-responsive operating parameters to a known initial value and places the pacemaker in a passive mode. In the passive mode the SIR signal does not control the pacing rate. The Auto-Set routine then displays instructions for the physician that cause diagnostic data to be collected. Such instructions effectively cause the pacemaker to be subjected to a known or predictable load. The Auto-Set routine then computes appropriate rate-responsive operating parameters that may be displayed for consideration by the physician, and/or that are automatically programmed into the pacemaker. The Auto-Set routine thus provides a method for automatically setting the programmable sensor parameters of the rate-responsive pacemaker based on a simple programming sequence performed by a physician.

22 Claims, 8 Drawing Sheets

SENSOR INDICATED RATE HISTOGRAM

Total Time Sampled: 0d 0h 1m 24s
Sampling Rate: 1.6 seconds

| | |
|---|---|
| Sensor | ON |
| Rate | 60 ppm |
| Maximum Sensor Rate | 120 ppm |
| Slope | 4 |
| Threshold | 3.5 |
| Reaction Time | MEDIUM |
| Recovery Time | MEDIUM |
| Measured Average Sensor | 3.7 |

Note: The above values were obtained when the histogram was interrogated.

| Bin Number | Range (ppm) | Time | Sample Counts |
|---|---|---|---|
| 1 | 60 – 68 | 0d 0h 0m 49s | 30 |
| 2 | 68 – 75 | 0d 0h 0m 36s | 22 |
| 3 | 75 – 83 | 0d 0h 0m 0s | 0 |
| 4 | 83 – 90 | 0d 0h 0m 0s | 0 |
| 5 | 90 – 98 | 0d 0h 0m 0s | 0 |
| 6 | 98 – 105 | 0d 0h 0m 0s | 0 |
| 7 | 105 – 113 | 0d 0h 0m 0s | 0 |
| 8 | 113 – 120 | 0d 0h 0m 0s | 0 |
| | | Total: | 50 |

Percent of Total Time

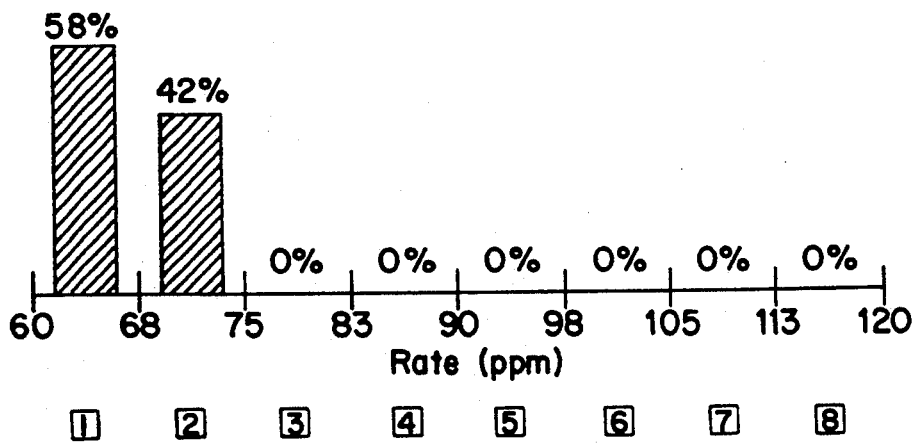

FIG. 4

SENSOR INDICATED RATE HISTOGRAM

Total Time Sampled: 0d 0h 1m 21s
Sampling Rate: 1.6 seconds

| | |
|---|---|
| Sensor | ON |
| Rate | 60 ppm |
| Maximum Sensor Rate | 120 ppm |
| Slope | 10 |
| Threshold | 3.5 |
| Reaction Time | MEDIUM |
| Recovery Time | MEDIUM |
| Measured Average Sensor | 3.7 |

Note: The above values were obtained when the histogram was interrogated.

| Bin Number | Range (ppm) | Time | Sample Counts |
|---|---|---|---|
| 1 | 60 – 68 | 0d 0h 0m 16s | 10 |
| 2 | 68 – 75 | 0d 0h 0m 28s | 17 |
| 3 | 75 – 83 | 0d 0h 0m 37s | 23 |
| 4 | 83 – 90 | 0d 0h 0m 0s | 0 |
| 5 | 90 – 98 | 0d 0h 0m 0s | 0 |
| 6 | 98 – 105 | 0d 0h 0m 0s | 0 |
| 7 | 105 – 113 | 0d 0h 0m 0s | 0 |
| 8 | 113 – 120 | 0d 0h 0m 0s | 0 |
| | | Total: | 50 |

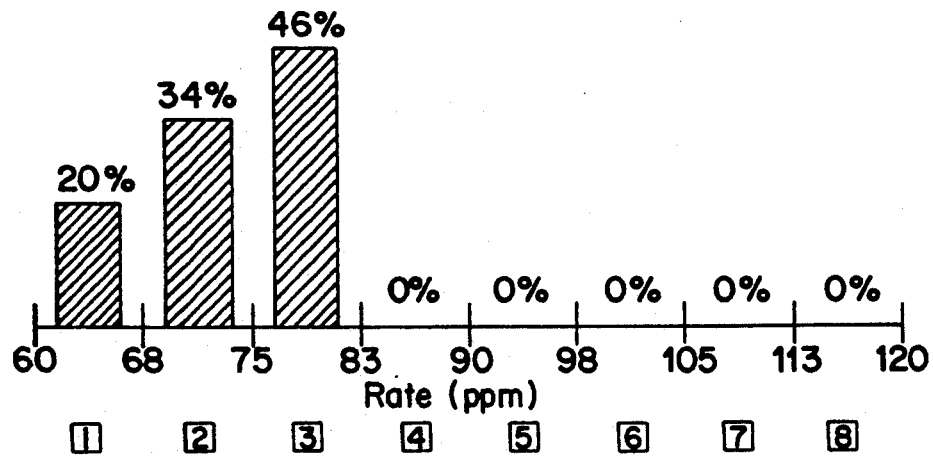

Note: Sensor Param. Changed Since Histogram Cleared

FIG. 5

METHOD AND SYSTEM FOR DETERMINING AND AUTOMATICALLY ADJUSTING THE SENSOR PARAMETERS OF A RATE-RESPONSIVE PACEMAKER

BACKGROUND OF THE INVENTION

1. Field of the Invention

The present invention relates to implantable medical devices and methods, and more particularly to a rate-responsive pacemaker and the manner in which such pacemaker is programmed in order to provide an optimum response for a particular patient.

A rate-responsive pacemaker is one wherein the pacing rate of the pacemaker (where the "pacing rate" is the rate at which the pacemaker provides stimulation pulses on demand) is adjusted automatically as a function of a sensed parameter. The parameter is measured by a sensor that may be included within the pacemaker or coupled to the pacemaker.

A common type of sensor used in rate-responsive pacemakers is an activity sensor that senses the physical activity level of the patient. Other types of sensors are also known, such as sensors that sense the blood oxygen level, the blood temperature, the blood pH, the respiration rate, or other parameters that indicate the need for a patient's heart to beat at a faster or slower rate.

The output signal from the sensor of a rate-responsive pacemaker is generally referred to as the "raw signal," or sometimes the "raw sensor input signal." The raw signal is processed in a prescribed manner by appropriate sensor processing circuits within the pacemaker in order to generate a sensor indicated rate (SIR) signal. The SIR signal, in turn, is utilized by the pacemaker processing circuits in order to define the pacing rate. Sometimes, the raw signal may be referred to as the "sensor input signal" (because it is the signal that is input into the sensor processing circuits of the pacemaker).

The manner in which the raw signal is processed by the sensor processing circuits is controlled by a plurality of sensor control parameters. Such control parameters define, for example, a threshold level above which the raw signal must reach before it is considered significant by the sensor processing circuits. Such parameters also define minimum and maximum SIR signals that define the lower and upper limits that the SIR signal may assume regardless of wide fluctuations in the raw signal, as well as the specific relationship that defines how the raw signal is converted to a specific SIR signal for values between the minimum and maximum SIR signals. The sensor control parameters may be fixed within the pacemaker or, as is more likely, may be programmed to desired values. Allowing the sensor control parameters to be programmed provides the physician with a technique for customizing the operation of a rate-responsive pacemaker for a particular patient.

For a more complete description of the general operation of a rate-responsive pacemaker, including the manner of programming such a pacemaker, and the typical sensor control parameters that may be utilized therein, reference is made to U.S. Pat. Nos. 4,712,555; 4,809,697; 4,940,052 and 4,940,053; which patents are incorporated herein by reference.

Disadvantageously, due to the number and interrelationship of sensor control parameters used in a modern rate-responsive pacemaker, the process of optimally programming such a pacemaker for a particular patient has become increasingly complex and difficult. The actual programming itself is not difficult nor complex, as modern programming aids, such as the analyzer-programmer system (APS), manufactured by Siemens Pacesetter, Inc. of Sylmar, Calif., have made programming any desired parameter into an implanted, programmable rate-responsive pacemaker as simple as following a sequence of menu screens displayed on the APS. The complexity and difficulty arises in knowing just what set of control parameters should be programmed for a particular patient in order to provide the most effective therapy. Such programming has become especially difficult as rate-responsive pacemakers have become more autonomic, controlled by inputs received from a multiplicity of internal sensors. What is needed, therefore, is a technique that assists a physician, or other medical personnel, in selecting an optimum set of sensor control parameters that may be programmed in a rate-responsive pacemaker.

A significant factor that makes the programming of a rate-responsive pacemaker so difficult is the variation in the sensor inputs from patient to patient. To appropriately program a rate-responsive pacemaker, a physician must anticipate how the pacemaker will respond in all conditions and activities that the patient is expected to exhibit. Because the physician, or other medical personnel, will not normally have sufficient information on which such programming decisions can be based, there is therefore a need for a tool or aid to assist the physician in anticipating the resultant pacemaker operation for each patient in activities that the particular patient will normally experience.

It is known in the art, as described, e.g., in U.S. Pat. No. 4,940,052, to collect SIR histogram data during the operation of a rate-responsive pacemaker, and to use such SIR histogram data as an aid to help program the sensor control parameters to appropriate values. However, such technique still requires gathering the SIR Histogram data, analyzing the SIR Histogram data to determine if the sensor control parameters are appropriately programmed, estimating how much the sensor control parameters should be changed, changing the sensor control parameters, re-gathering new SIR Histogram data based on the newly programmed sensor control parameters, and then re-analyzing the SIR Histogram data to determine if the sensor control parameters have been changed an appropriate amount. This process is repeated over and over again until the physician is convinced that the SIR Histogram data reflects an appropriate programming of the sensor control parameters. Unfortunately, such process typically requires several iterations, and is therefore very time consuming. Moreover, the process still involves a significant amount of guess work, or trial-and-error, in order to zero in on an optimum setting of the sensor control parameters. What is needed, therefore, is an improved technique for using the SIR Histogram data that simplifies and shortens the programming process, and minimizes the trial-and-error (guesswork) that has previously accompanied sensor parameter programming.

The present invention advantageously addresses the above and other needs.

SUMMARY OF THE INVENTION

The present invention provides a rate-responsive pacing system in which the many interrelated operating parameters associated with a rate-responsive mode of operation may be automatically and/or optimally set for a particular patient. The system includes both an implantable rate-responsive pacemaker and an external programming device. The rate-responsive pacemaker includes an suitable sensor for monitoring a prescribed parameter in order to provide a measure for how fast the patient's heart should beat. The pacemaker also includes appropriate memory circuits for recording a sensor indicated rate (SIR) signal derived from the sensor, so as to provide SIR histogram data, regardless of whether the pacemaker is programmed to use the SIR signal to control the pacing rate. The external programming device includes means for establishing an RF telemetry link with the implantable pacemaker so that the SIR histogram data, as well as other data associated with the operation of the pacemaker, can be retrieved. Such RF telemetry link provides a means whereby the implantable pacemaker can be programmed with appropriate operating parameters. The external programmer also includes processing means for processing the SIR histogram and other data so as to assist in programming the sensor.

In accordance with one aspect of the invention, an autoset routine or sequence (hereafter "Auto-Set") is selectively carried out by the external programming device when in contact with the implantable pacemaker through the RF telemetry link. Such Auto-Set routine or sequence sets all of the rate-responsive operating parameters to a known initial value and places the sensor of the pacemaker in a PASSIVE mode so that the SIR signal does not control the pacing rate. (Note that this particular step, while a part of the preferred embodiment, is not necessarily required and may optionally not be used.) The Auto-Set routine then displays simple instructions to the physician (or other medical personnel using the programming device) that cause diagnostic data to be collected. Such instructions, in effect, subject the pacemaker to a known or predictable load. After the diagnostic data is collected, the Auto-Set routine computes appropriate rate-responsive operating parameters that could be used with the pacemaker to provide an optimum performance. Such operating parameters are displayed for consideration by the physician. As selected by the physician, such operating parameters may then be programmed into the pacemaker. In one embodiment, the computed operating parameters are automatically programmed into the pacemaker.

The present invention thus also provides a method for automatically setting the programmable parameters of a rate-responsive pacemaker based on a simple programming sequence performed by a physician. Basically, the method involves having the patient within whom the rate-responsive pacemaker has been implanted perform some specified task, such as walking around the room, or up a flight of stairs, thereby placing an identifiable load on the patient's cardiovascular system at a time when a known set of parameters are programmed in the pacemaker. During the performance of the specified task, the pacemaker sensor is in a PASSIVE mode, meaning that the memory circuits in the pacemaker record the sensor indicated rate (SIR) signal derived from the sensor, but the SIR signal does not control the pacing rate. Other relevant pacing data, such as the actual paced rate or natural heart rate (if not paced) may also be recorded while performing the specified task. From the SIR signal data, which the physician retrieves from the pacemaker memory circuits after the task has been completed (using an external programming device coupled to the pacemaker by an RF telemetry link), and with a knowledge of the physiological stress level associated with the specified task, the physician selects a desired sensor rate for the task that was performed. The programming device then computes a suggested set of programmable parameters that will best achieve the desired sensor rate. Such suggested set of programmable parameters may then be manually or automatically programmed into the pacemaker.

One embodiment of the present invention may thus be characterized as a rate-responsive pacing system. Such system comprises both an implantable rate-responsive pacemaker and an external programming device. The rate-responsive pacemaker of such system includes: (a) sensing means for sensing natural contractions of a heart; (b) stimulation means for generating stimulation pulses for delivery to the heart at a prescribed pacing rate in the absence of sensed natural contractions; (c) physiological sensor means for sensing a physiological parameter and generating a sensor indicated rate (SIR) signal as a function thereof; (d) control means for defining said prescribed pacing rate as a selected one of either a programmed pacing rate value or the SIR signal; and (e) counting means for counting and storing each occurrence of the SIR signal that falls within one of a plurality of rate ranges, thereby collecting SIR histogram data within the rate-responsive pacemaker.

The external programming device of such rate-responsive system includes: (a) telemetry means for establishing an RF telemetry link with the implantable pacemaker through which event data representative of the specified events counted and stored within the rate-responsive pacemaker, including the SIR histogram data, may be retrieved; (b) programming means for programming selected control data into the rate-responsive pacemaker through the RF telemetry link, the control data including the programmed value of the pacing rate, an indication of whether the programmed value or the SIR signal is to be used to define the pacing rate, and a set of SIR control parameters that define the manner in which the SIR signal is generated from the physiological parameter sensed by the physiological sensor means; and (c) processing means for processing the SIR histogram data so as to produce a recommended set of SIR control parameters for controlling the rate-responsive pacemaker.

The present invention may also be characterized as an Auto-Set system for use within an external programming device in contact with an implantable rate-responsive pacemaker through an RF telemetry link. The rate-responsive pacemaker and external programming device are substantially as described above. The Auto-Set system used with such pacemaker and programming device, when invoked, performs the following three functions:

1. Sets a set of control parameters, including the SIR control parameters, to known initial values. These control parameters cause the rate-responsive pacemaker to assume a passive mode wherein the SIR signal is generated but is not used to define the rate at which stimulation pulses are generated.
2. Gathers diagnostic data using the rate-responsive pacemaker under known conditions. Such diagnostic data includes the count of the SIR signals during the time that the control parameters assumed the known initial values.

3. Processes the diagnostic data in order to define a set of SIR control parameters that optimally define the manner in which the SIR signal is derived from the sensor for the particular environment underwhich the diagnostic data was gathered.

Processing of the diagnostic data by the Auto-Set system (step 3 above) involves the steps of: (a) determining a plurality of potential heart rate values that could have been the SIR rate value for the heart load condition existing at the time the diagnostic data was collected; (b) allowing the physician (or other medical personnel) to select a desired heart rate value from the list of potential heart rate values; and (c) using the selected desired heart rate value to point to a set of optimum SIR control parameters.

Further, it should be noted that the present invention may also be characterized as a method for determining a proposed set of programmable parameters of a rate-responsive pacemaker implanted within a patient. Such method includes the steps of:

(a) Setting the programmable parameters within the pacemaker to a set of specified initial values. Such specified initial values cause the pacemaker to assume a passive mode wherein the sensor indicated rate (SIR) data generated within the pacemaker does not influence the operation of the rate-responsive pacemaker.

(b) Instructing the patient within whom the rate-responsive pacemaker has been implanted to perform a specified task.

(c) Storing the SIR data in the rate-responsive pacemaker while the task specified in step (b) is being performed.

(d) Estimating a desired sensor indicated rate for the rate-responsive pacemaker for the specified task performed in step (b).

(e) Processing the SIR data stored in step (c) and the desired sensor indicated rate estimated in step (d) to determine a suggested set of programmable parameters for use within the rate-responsive pacemaker.

It is thus a goal of the present invention to simplify the way in which the sensor parameters of a rate-responsive pacemaker are set. More particularly, it is a goal of the invention to provide a technique for setting the sensor parameters of a rate-responsive pacemaker that removes much of the guess work that has heretofore accompanied such task.

It is a feature of the invention to provide a programming tool or aid for use by a physician, or other medical personnel, that allows the physician to accurately predict the expected behavior of an implanted rate-responsive pacemaker with a given programmed state, and that facilitates the programming of the pacemaker in such state.

It is another feature of the invention to provide a technique for setting the sensor parameters of a rate-responsive pacemaker that sets the parameters based on what a physician wants to see happen for a particular patient, i.e., that sets the parameters to provide a given sensor indicated rate for a well-defined level of exercise.

BRIEF DESCRIPTION OF THE DRAWINGS

The above and other aspects, features and advantages of the present invention will be more apparent from the following more particular description thereof, presented in conjunction with the following drawings wherein:

FIG. 4 illustrates representative SIR histogram data for one set of sensor parameters;

FIG. 5 illustrates representative SIR histogram data using the same set of sensor parameters as in FIG. 4 except for a different slope value;

Figure 1:
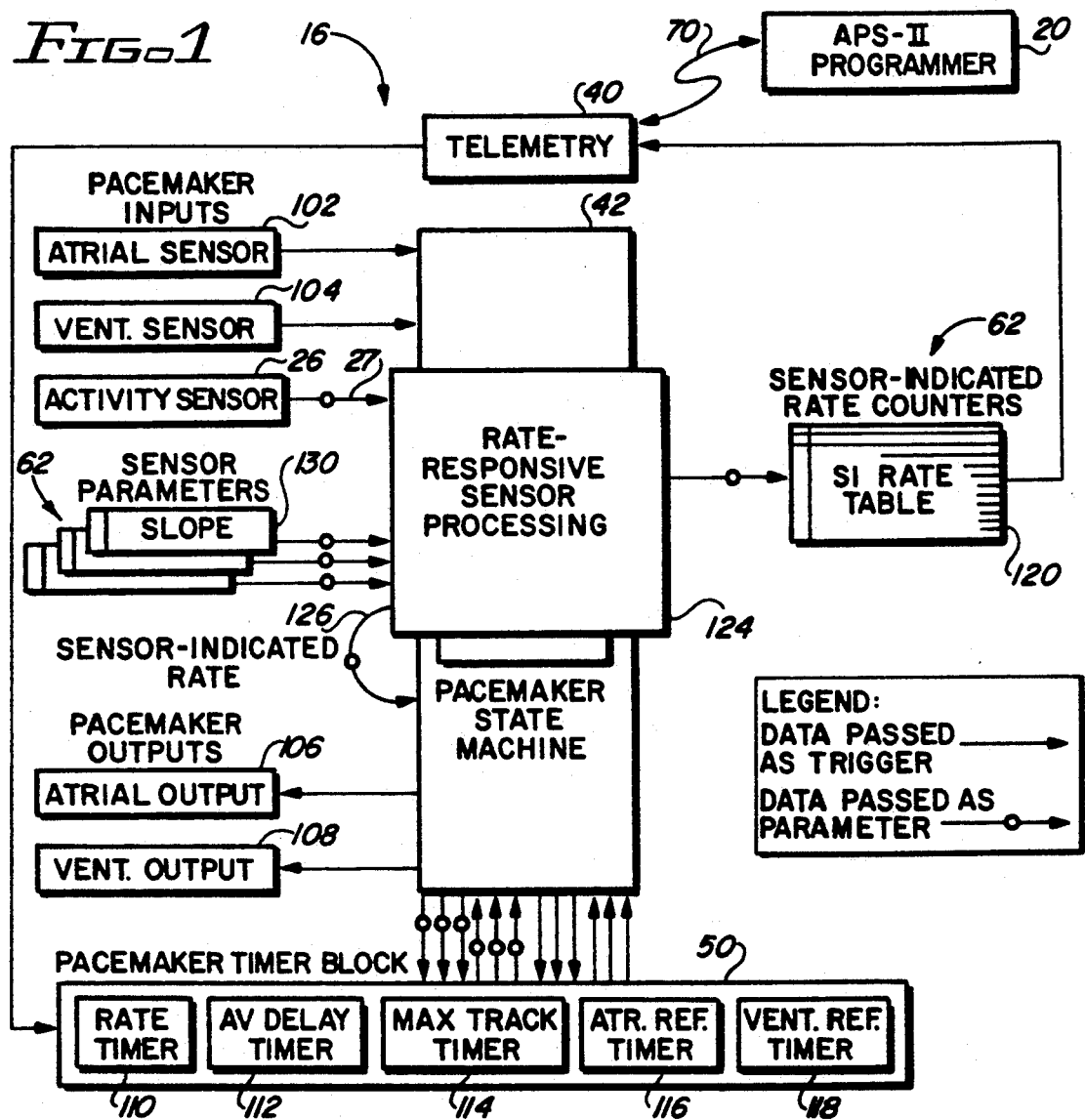
FIG. 1 shows a block diagram of a rate-responsive pacemaker.

Appendix A is a Table that lists the primary programs and routines, and their respective functions, inputs and outputs, used within the programming device in order to carry out the Auto-Set method of the present invention;

Appendix B shows an Auto-Set Delta Rate algorithm used by the Auto-Set method of the invention; and Appendix C is a Table used by the Auto-Set Delta Rate algorithm shown in Appendix B.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention relates to a system and method of automatically setting or programming the sensor parameters of a rate-responsive pacemaker. Before describing the invention, and in order to better understand the description of the invention that follows, it will first be helpful to have a basic understanding of how a rate-responsive pacemaker operates, as well as an understanding of how such a pacemaker is programmed. Accordingly, an overview of the operation of a rate-responsive pacemaker will first be presented, including a description of the programmable sensor parameters that are used with such a rate-responsive pacemaker. More complete details associated with the rate-responsive pacemaker used with the present invention, as well as the preferred programmer used to program such pacemaker may be found in U.S. Pat. Nos. 4,809,697 and 4,940,052, previously incorporated herein by reference. Further, reference is also made to the following copending and commonly owned U.S. patent applications (1) Ser. No. 07/846,461, filed concurrently herewith, entitled METHOD AND SYSTEM FOR RECORDING AND REPORTING THE DISTRIBUTION OF PACING EVENTS OVER TIME; (2) Ser. No. 07/846,460, filed concurrently herewith, entitled METHOD AND SYSTEM FOR RECORDING AND REPORTING A SEQUENTIAL SERIES OF PACING EVENTS; and (3) Ser. No. 07/844,807, also filed concurrently herewith, entitled RATE-RESPONSIVE PACEMAKER HAVING AUTOMATIC SENSOR THRESHOLD WITH PROGRAMMABLE OFFSET. Each of the above-identified U.S. Patent Applications are also incorporated herein by reference.

Referring first to FIG. 1, there is shown a functional block diagram of a rate-responsive pacemaker 16 that illustrates the manner in which the pacemaker collects the sensor indicated rate (SIR) counts that are used with the present invention. The pacemaker 16 includes pacemaker state logic 42, also referred to as the pacemaker state machine. Coupled to the state machine 42 are the pacemaker timer circuits 50, also referred to as the pacemaker timer block. The pacemaker 16 receives as inputs, i.e., signals sensed by the pacemaker that are not programmed, an atrial sensor 102 and a ventricular sensor 104. The atrial sensor 102 and ventricular sensor 104 sense P-waves and R-waves, evidencing the natural contraction of the atria or ventricles, respectively. The atrial sensor 102, for example, may include an atrial tip electrode, an atrial lead 31 and atrial channel amplifier 48 (not shown). Similarly, the ventricular sensor 104 may comprise a ventricular tip electrode, a ventricular lead and a ventricular amplifier.

The inputs to the rate-responsive pacemaker 16 also include a sensor input raw signal 27 obtained from a physiological sensor 26. (It is noted that while only a single physiological sensor 26 is shown in FIG. 1, more than one such sensor may be used, each providing its own sensor input.) The raw signal 26 is input to a rate-responsive sensor processing circuit 124. After appropriate processing, as described more fully below, the sensor processing circuit 124 provides a sensor indicated rate (SIR) signal 126 to the pacemaker state machine 42.

In addition to the above-described pacemaker inputs, there are several pacemaker control parameters that are input to the pacemaker state machine 42 in order to control its operation in a desired fashion. Such control parameters are normally programmed into the pacemaker 16 using an external programmer 20, such as the APS-II/MTM external programmer manufactured by Siemens Pacesetter, Inc. of Sylmar, Calif., that establishes a telemetry link 70 with a telemetry circuit 40 included within the pacemaker 16.

The parameters programmed into the pacemaker are typically stored in a memory 62 of the pacemaker 16. (The memory 62 is not shown as a separate block in FIG. 1, but it is to be understood that the programmed parameters may be held in such memory, as may output data generated by the pacemaker that is to be telemetered to the programmer 20.) Such control parameters include, e.g., the programmed rate at the which the stimulation pulses are to be generated by the pacemaker (used to define various time periods within the time block 50), the particular mode of operation of the pacemaker, a set of sensor control parameters 130 (described below), and the like.

The rate-responsive pacemaker outputs, i.e., signals generated by the pacemaker state machine 42 in response to the pacemaker inputs and/or pacemaker control parameters include an atrial output 106 and a ventricular output 108. The atrial output 106 provides an atrial stimulation pulse ("A-pulse") for delivery to the atrium at an appropriate time, e.g., on demand as needed to maintain a programmed or sensor-indicated heart rate. The ventricular output 108 similarly provides a ventricular stimulation pulse ("V-pulse") for delivery to the ventricle at an appropriate time, e.g., on demand as needed to maintain a programmed or sensor-indicated heart rate.

The pacemaker timer circuits 50 include at least five separate timers. A rate timer 110 determines or measures the pacing cycle duration. An AV Delay Timer 112 defines the time period between an A-pulse and a V-pulse. A Max Track Timer 114 defines the time period of the maximum rate at which the pacemaker is allowed to provide stimulation pulses, i.e., it defines the maximum paced rate. An Atrial Refractory Timer 116 defines the atrial refractory period (i.e., that time period during which the atrial channel is refractory). Similarly, a Ventricular Refractory Timer 118 defines the ventricular refractory period, or that time during which the ventricular channel is refractory.

Note from the symbols used in FIG. 1 that two kinds of data are passed to and from the pacemaker state machine 42. Such data may take the form of a trigger signal or a parameter signal. A trigger signal, represented by an input line with an arrow pointing the direction of flow of the trigger data, is a signal that operates substantially immediately, much like an interrupt signal, to bring about a desired result. That is, for example, immediately upon sensing atrial activity through the atrial sensor (or within one or two clock cycles thereafter, where a clock cycle is typically on the order of a few microseconds), the state of the state machine 42 changes appropriately to bring about a desired result. In contrast, a parameter signal, represented by an input line passing through a circle with an arrow pointing the direction of flow of the parameter data, is a signal that is made available to the state machine 42 for use at the appropriate time during the normal timing cycle of the state machine.

In accordance with the present invention, the rate-responsive sensor processing circuits 124 receive the raw signal 27 from the sensor 26 and derive a SIR signal 126 therefrom based on a set of sensor control parameters 130. The SIR signal 126 may then be used by the state machine 42, if so programmed, to control the rate at which stimulation pulses are provided to the heart through the atrial or ventricular outputs 106 and 108. The SIR signal 126 is sampled at a fixed, but programmable rate (which may be, e.g., every event, every 1.6 seconds, or every 26 seconds). The SIR signal as sampled is classified by rate and stored in an SIR Table 120. The SIR Table 120 is made up of a plurality of counters, each assigned to a different rate range, that count each occurrence of an SIR rate signal that is within the rate range assigned to the counter. Thus, each counter of the Table 120 may be considered as a "bin" wherein a count is maintained of the SIR signals that occur within the assigned range, with the collection of all of such bin data over time thereby providing SIR histogram data.

It is noted that the collection of SIR histogram data as suggested in FIG. 1 is fully described in the '052 patent cited above, and is not the subject of the present invention. Rather, the present invention uses the SIR histogram data thus generated and processes it in a manner so as to derive a proposed set of sensor control parameters 130 that may be programmed into the rate-responsive pacemaker 16 in order to optimally control it for a particular patient.

Figure 2:
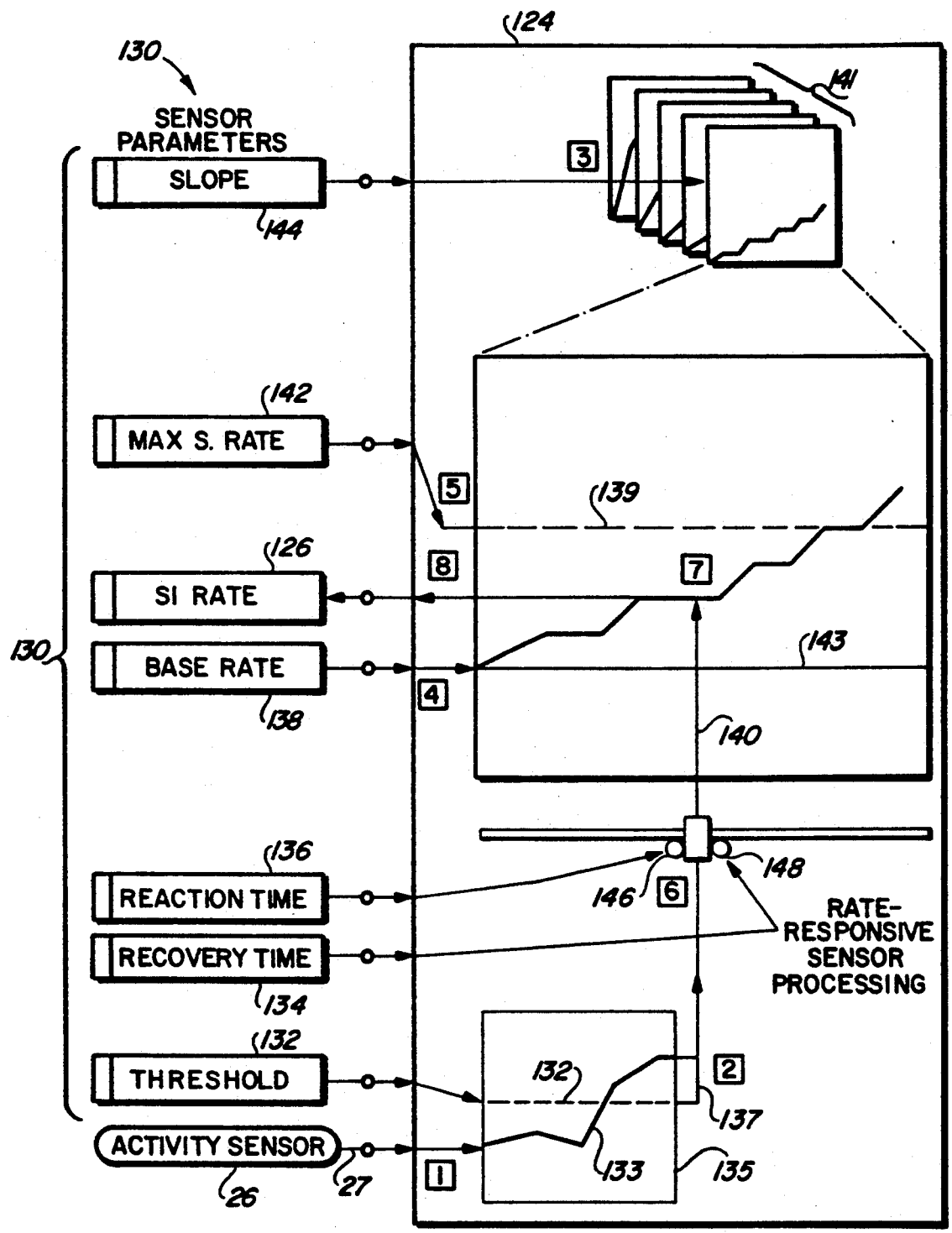
FIG. 2 is a block diagram of the rate-responsive processing subsystem of FIG. 1, and functionally illustrates the parametric controls used to adjust the sensor indicated rate (SIR) signal as a function of the raw sensor input signal.

The sensor control parameters that may be programmed in a rate-responsive pacemaker 16 are functionally illustrated in FIG. 2. FIG. 2 shows a functional block diagram of the rate-responsive processing subsystem 124 of the rate-responsive pacemaker 16 of FIG. 1. FIG. 2 shows the set of sensor control parameters 130 that are used to adjust the sensor indicated rate (SIR) signal 126, and diagrammatically illustrates how such adjustment is accomplished as a function of the raw signal 27. As seen in FIG. 2, there are seven sensor control parameters: a Threshold parameter 132; a Recovery Time parameter 134; a Reaction Time parameter 136; a Base Rate parameter 138; a Sensor Indicated Rate (SIR) parameter or signal 126; a Maximum Sensor Rate parameter 142; and Slope parameters 144. These control parameters are explained more fully below.

The sensor 26 (which is illustrated in FIG. 1 and FIG. 2 as an "activity sensor"; but which may be another type of physiological sensor, or combination of physiological sensors) generates a raw signal 27 in response to detected physiological stress in the patient. The raw signal 27 is processed in an appropriate manner, e.g., to determine the energy content thereof as taught in the '053 patent cited above, in order to provide a suitable sensor input signal 133 that may be processed by the rate-responsive sensor processing subsystem 124. The processed signal 133 will thus vary as a function of time, as suggested by the graph 135, as the physiological stress of the patient varies as detected by the sensor 26.

The Threshold parameter 132 defines the level above which the physiological stress, e.g., activity, as determined by the sensor 26, must rise before it is considered significant. Once the stress level has risen above the Threshold 132, then the amount that it exceeds the Threshold is used as an input to the rate-responsive sensor processing subsystem 124. This amount (the amount above the Threshold 132) is schematically represented in FIG. 2 as the shaded area 137 at the time corresponding to the right edge of the graph 135.

The Slope parameter 144 defines the relationship between the amount the sensor input signal is above the Threshold 132 and the increase or decrease in pacing rate. That is, the Slope parameter may be considered, as its name implies, as a curve or transfer function that converts that portion 137 of the sensor input signal above the Threshold level to the sensor indicated rate (SIR) signal 126. There are a multiplicity of possible Slope parameters or curves 144 that may be selected, each one providing a different rate increase in response to sensed physiological stress above the Threshold. Such multiplicity of Slope parameters 144 are schematically represented in FIG. 2 as the family of Slope curves 141.

The Maximum Sensor Rate parameter 142 defines the upper limit of the rate range of the rate-responsive pacemaker 16. The pacemaker will not pace above this rate, regardless of the amount by which the sensor input signal exceeds the threshold 132. Such upper limit is schematically represented in FIG. 2 as the dotted line 139.

The Base Rate parameter 138 defines the lower limit of the rate range of the rate-responsive pacemaker 16. The pacemaker will not pace below this rate, regardless of how close the sensor input signal comes to the Threshold 132. When the pacemaker is pacing at the base rate, the patient is at rest or undergoing physiological stress at a level below the Threshold limit. Such lower limit is schematically represented in FIG. 2 as the solid line 143.

Still referring to FIG. 2, the Reaction Time parameter 136 determines the minimum time to be allowed for an increase in pacing rate from the Base Rate to the programmed Maximum Rate. The Reaction Time controls the amount of time the pacemaker spends at a given pacing rate by requiring a minimum number of stimulation pulses at that rate. Once these pulses occur, the rate can be increased. A short Reaction Time allows the pacing rate to accelerate rapidly in response to sensed physiological activity above the Threshold; a long Reaction Time forces a slow increase in the pacing rate.

The Recovery time parameter determines the minimum time allowed for a decrease in pacing rate from the programmed Maximum Rate to the Base Rate. It uses the same principle as the Reaction Time. That is, it controls the amount of time the pacemaker spends at a given pacing rate by requiring a minimum number of stimulation pulses before the rate can be decreased. A short Recovery Time allows a rapid deceleration of the pacing rate; a long Recovery Time forces a slower decrease in pacing rate.

In operation, the sensor 26 senses physiological activity and generates a raw signal 27 in response thereto. The raw signal 27 is processed in an appropriate manner in order to produce the sensor input signal 133. The amount 137 by which the sensor input signal 133 exceeds the programmed Threshold 132, in conjunction with the Reaction Time 136, provides a sensor index signal 140 that points to a specific entry point on one axis of the selected Slope curve 144. The Reaction Time 136 determines how rapidly the sensor index signal moves along the selected Slope curve 144 towards the Maximum Rate 139. If the number of pulses at the current SIR signal 126 has reached the amount required by the Reaction Time, the SIR may be increased to its next value, as defined by the current value of the SIR rate 126, and limited by the Maximum Sensor Rate 139. If the Reaction Time pulse count has not been reached, the SIR signal will not change.

If no sensor input signal is detected as being above the Threshold 132, and if this lack of activity has occurred for the number of pulses specified by the Recovery Time parameter, the SIR signal may be decreased to its next value as defined by the selected Slope curve and as limited by the Base Rate parameter 138. If the Recovery Time pulse count has not been reached, the SIR signal will not change.

Note, as described above, that the Reaction Time 136 controls the rate of increase of the SIR signal 126, and hence the rate of increase of the pacing rate. The Recovery Time 134 controls the rate of decrease of the SIR signal 126, and hence the rate of decrease of the pacing rate. The Reaction Time 136 is schematically illustrated in FIG. 2 as a roller 146 that controls how fast the sensor index signal 140 is allowed to move left-to-right along the horizontal axis of the selected Slope curve 144. Similarly, the Recovery Time 134 is schematically illustrated in FIG. 2 as a roller 148 that controls how fast the sensor index signal 140 is allowed to move right-to-left along the horizontal axis of the selected Slope curve 144.

Figure 3:
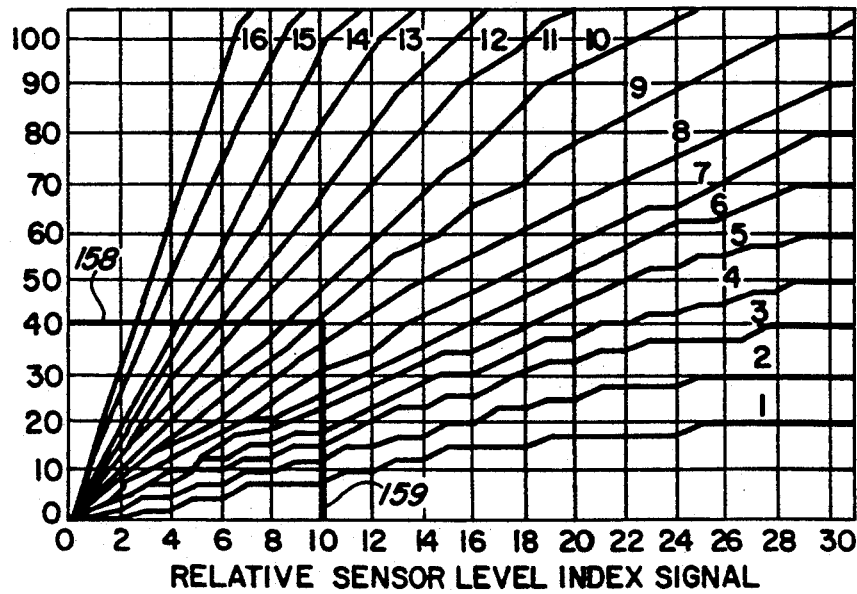
FIG. 3 illustrates a family of slope curves that define the transfer function between a sensor level index and the SIR signal.

In the preferred embodiment, there are sixteen Slope parameters or curves 144 that may be selected for use within the rate-responsive pacemaker 16. All sixteen of such Slope curves 144 are illustrated in FIG. 3. The horizontal axis of the family of curves shown in FIG. 3 is a relative sensor level index signal. Depending upon the type of sensor 26 that is used, the range of possible outputs from the sensor, ranging from no physiological stress to high physiological stress, are divided into 32 discrete steps, labeled 0 through 31. The number at any particular point along the horizontal axis is referred to as the sensor index at that point.

The vertical axis of the family of curves shown in FIG. 3 is a relative SIR pacing rate. The relative SIR pacing rate is measured relative to the Base Rate 128.

To illustrate the manner in which the family of Slope curves in FIG. 3 is used, suppose that the Slope curve "9" has been selected as the Slope curve to be used by the rate-responsive pacemaker 16. If the amount of the sensor input signal above the Threshold parameter corresponds to a sensor index of "10," then the relative SIR signal, corresponding to the Slope curve "9," is "40" ppm, or 40 ppm above the Base Rate. Thus, if the Base Rate is programmed at 60 ppm, and assuming a sensor index of "10" and a programmed Slope Curve "9," the SIR signal would be 100 ppm, as indicated by the bold lines 158 and 159 in FIG. 3.

In operation, the family of Slope curves shown in FIG. 3, or other desired Slope curves, is programmed into the pacemaker memory circuits. Such programming may be accomplished by way of a look-up Table, or by way of an appropriate algorithm, that maps a given Sensor Index signal to a relative SIR signal for each Slope curve selected.

It should be pointed out that while the above description of the sensor control parameters in conjunction with FIG. 2 and FIG. 3 assumes that only one sensor 26 and one raw signal 27 is generated, the invention is not so limited. Indeed, several sensors could be employed, each generating its own raw signal; which raw signals may then be appropriately processed and combined so as to provide a composite sensor input signal that may be used by the rate-responsive sensor processing subsystem 124 of the invention.

Turning next to FIG. 4, representative SIR histogram data for one set of sensor control parameters is illustrated. Such histogram data may be gathered and displayed in the manner described in the '052 patent. The sensor control parameters used to collect such SIR histogram data are also included with the histogram data and are displayed at the top of FIG. 4. Such sensor control parameters include a Base Rate of 60 ppm, a Maximum Sensor Rate of 120 ppm, a Slope Curve of 4 (meaning that Slope curve Number 4 was selected, as shown in FIG. 3), a Threshold value of 3.5, and Reaction and Recovery Times of "Medium." The Threshold value of 3.5 is expressed in the same units as the Sensor Input signal, which (depending upon the type of sensor 26 that is used) may be volts, millivolts, milliseconds, per cent, etc. For an activity sensor that is realized using a piezoelectric crystal, such units are in millivolts. Note that the average sensor input signal measured during the time the SIR Histogram data was collected is also computed and displayed. For the example shown in FIG. 4, such average sensor input signal was 3.7, just above the sensor Threshold of 3.5.

The Histogram data shown in FIG. 4, which was collected as the patient performed a specified exercise, indicates that 58% of the time was spent pacing at a rate of between 60 and 68 ppm (Bin 1), and that the remaining time (42%) was spent pacing at a rate of between 68 and 75 ppm (Bin 2). By analyzing this distribution of the SIR data, a physician might conclude that a higher SIR rate would better serve this patient at his level of exercise. A higher SIR rate could be obtained by selecting another Slope curve, one that would provide a higher relative SIR rate for the same sensor index inputs. Accordingly, the Slope curve was reprogrammed to 10, and a second exercise was performed by the patient.

The SIR Histogram data obtained for the second exercise is shown in FIG. 5. Such data indicates that 46% of the time was spent pacing at a rate of between 75 and 83 ppm (Bin 3), 34% of the time was spent pacing at a rate of between 68 and 75 ppm (Bin 2), and 20% of the time was spent pacing at a rate of between 60 and 68 ppm (Bin 1). A physician might conclude that such distribution of pacing rates for the particular patient who performed the exercise would be a more desirable response. On the other hand, the physician might determine that still a higher peak SIR signal would be best, in which case a still higher Slope parameter would have to be reprogrammed and the SIR Histogram data would have to be collected and analyzed again. Alternatively or conjunctively, the physician might determine that the Threshold or Recovery or Reaction Times were not quite right for the particular patient involved, in which case still additional reprogramming and retesting would have to be performed.

The process described above in connection with FIG. 4 and FIG. 5 is essentially the approach used to adjust the sensor control parameters as described in the '052 patent. The availability of the SIR Histogram data represents a significant advance in the art over the prior approaches used to program rate-responsive pacemakers. However, even with the SIR Histogram data, the process leaves much to be desired relative to ascertaining quickly an optimum set of control parameters for a particular patient.

Advantageously, the present invention provides a technique that addresses the above-identified need in that it quickly presents to the physician a proposed set of sensor control parameters that will achieve a desired SIR rate for the particular patient at a given and known level of exercise. The technique is referred to hereafter as the "Auto-Set" sequence or method. This name is used because the technique automatically sets the control parameters (or at least proposes the control parameters that may, upon review, be set) to the values needed to achieve a desired response in the particular patient within whom the rate-responsive pacemaker is implanted.

Figure 6:
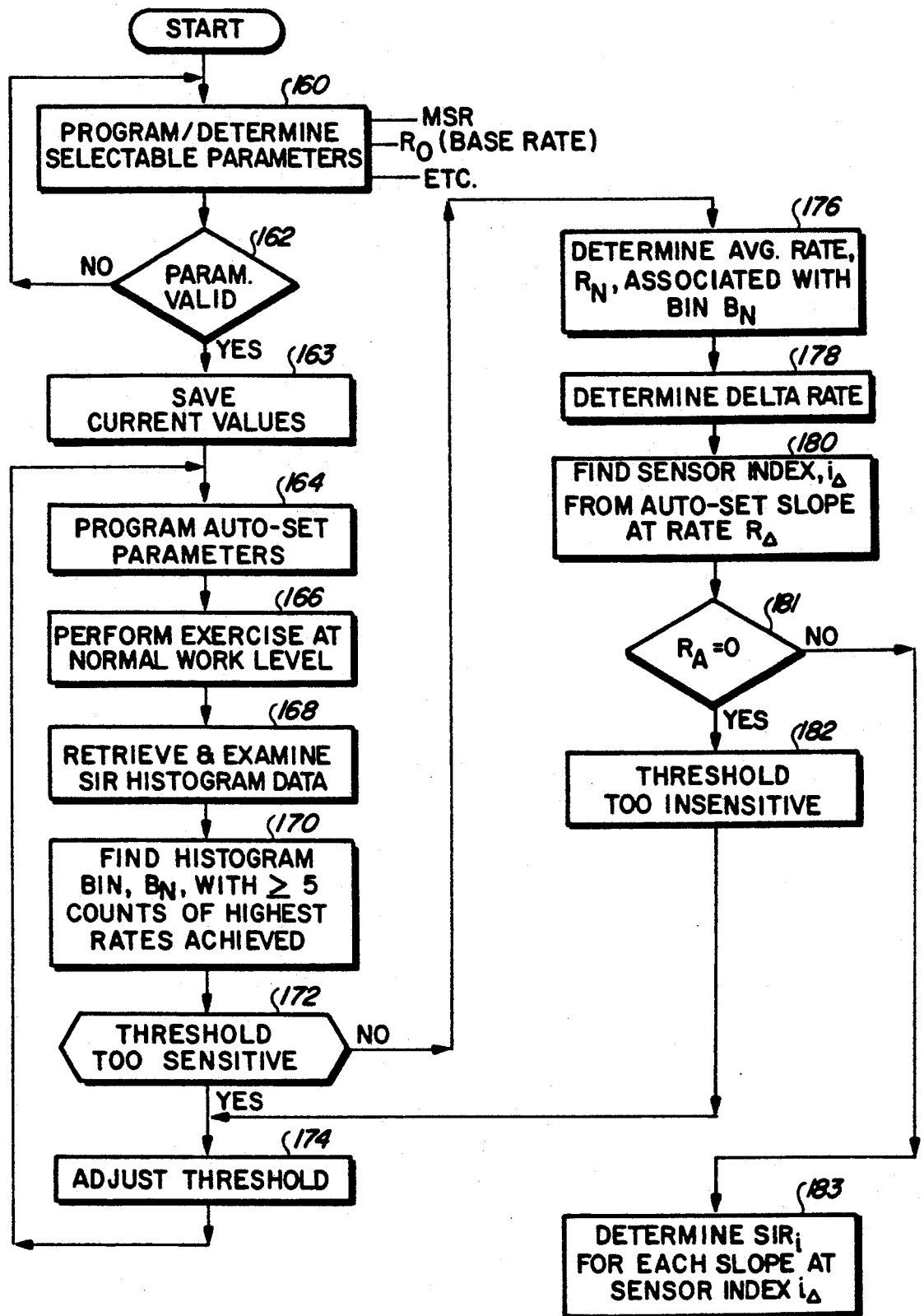
FIGS. 6 and 7 are flowcharts of the Auto-Set method of the present invention.
Figure 7:
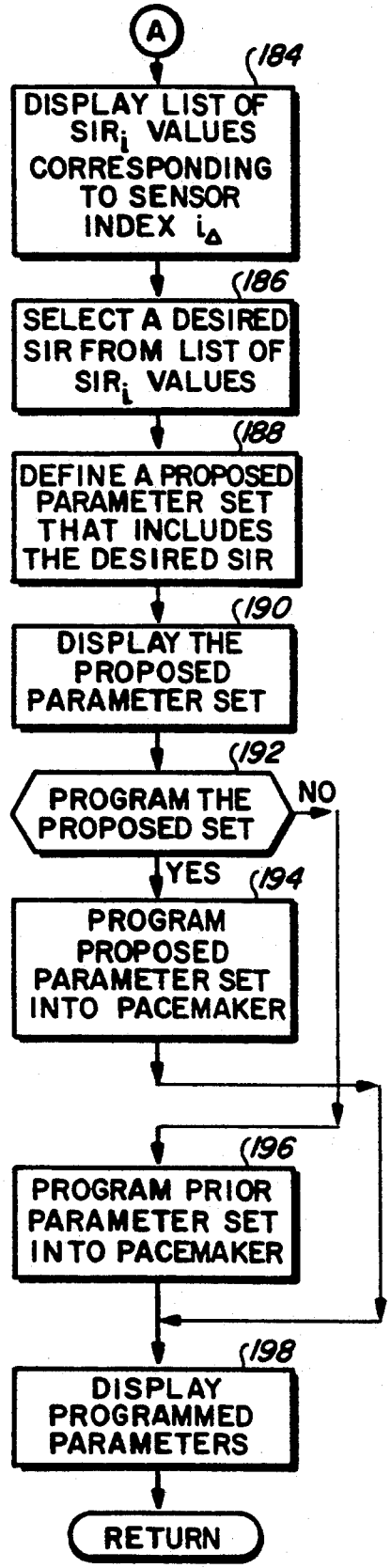

FIG. 6 and FIG. 7 show a flowchart of the Auto-Set sequence of the present invention. Different portions of the same flow chart are shown on each of FIG. 6 or FIG. 7. (That is, the flowchart is too large to fit on a single drawing sheet.) Each main step of the method shown in FIG. 6 or FIG. 7 is shown as a block, or box, with each block having a reference numeral assigned thereto.

The rate-responsive pacemaker used with the Auto-Set sequence or method shown in FIGS. 6 and 7 may be as described above in connection with FIG. 1 and FIG. 2. That is, the pacemaker includes the ability to collect SIR Histogram data, as well as the ability to programmably select a desired set of sensor control parameters. The pacemaker also includes the ability to program the sensor 26 ON, OFF, or PASSIVE. When the sensor is programmed ON, the SIR signal generated by the rate-responsive sensor processing subsystem 124 is used by the state machine 42 of the pacemaker to control the rate at which stimulation pulses are provided. When the sensor is programmed OFF, the rate-responsive pacing subsystem 124 is effectively turned OFF, and has no influence on the operation of the pacemaker. When the sensor is programmed PASSIVE, the rate-responsive pacing subsystem 124 operates, and the SIR signal is stored in the SIR Table 120 (i.e., SIR Histogram data is collected at the programmed sampling rate, which may be, e.g., every 1.6 seconds or every 26 seconds), but the SIR signal is not used to control the operation of the pacemaker.

The programmer used with the method or sequence shown in FIGS. 6 and 7 may be substantially as described in the '697 patent, as least insofar as its hardware is concerned, or in the above-referenced copending patent applications. That is, the programmer 20 is preferably an APS-II/MTM programmer that includes the ability to establish a telecommunicative link 70 with the pacemaker for the purpose of downloading the SIR Histogram data, as well as for the purpose of programming the sensor control parameters into the pacemaker circuits. The programmer includes a display upon which various data and instructions may be presented. The programmer also includes a processor, or equivalent processing circuitry, for analyzing the SIR Histogram data that is retrieved and for performing rudimentary calculations associated with the Auto-Set sequence of the present invention.

The Auto-Set sequence advantageously allows the physician, or other medical personnel using the programmer 20 (hereafter the "operator"), to determine the optimal Slope curve or value for the patient. The Auto-Set sequence is further of assistance in setting the Maximum Sensor Rate, Threshold, and other Sensor Parameters, when necessary.

During the Auto-Set sequence, the patient is required to perform a measured level of exercise, during which time the SIR Histogram counters of the pacemaker are updated. The SIR Histogram data is then used to determine a Normal Work Rate and to compute the corresponding rates of all applicable Slope parameters. The operator is then prompted to select a Desired Rate which best fits the patient's activity. Based on the Desired Rate selected, the corresponding Slope is then suggested by the Auto-Set sequence.

Turning then to FIG. 6, a preliminary step of the Auto-Set sequence, after establishing a telecommunicative link with the implantable pacemaker 16, involves programming or otherwise determining the selectable parameters associated with the sensor control parameters (block 160). The pacemaker will always have some sensor control parameter values programmed therein, even if only default values. Hence, once the telecommunicative link is established with the pacemaker, the pacemaker will be interrogated to determine what the control parameters are. If any of the parameters Base Rate (referred to as $R_0$), Sensor (ON, OFF, or PASSIVE), MSR, Slope (1-16), Threshold, Reaction Time, or Recovery Time, are unknown or invalid, or cannot be determined through re-interrogation of the pacemaker, the operator will be prompted to provide them. Thus, the operator may be prompted to provide some of the control parameters.

Once the control parameters have been selected, or otherwise determined, a determination is made as to whether such parameters are valid (block 62). The control parameter values could be invalid, for example, if not within prescribed limits. (For example, the Base Rate may not be greater than certain limits, and the MSR may not be less than other limits, the Slope must have a value of from 1 to 16, and the Threshold must be within prescribed limits.) If the values are valid, they are saved in the memory of the programmer (block 163). Also saved is the current SIR Histogram Sampling Rate (1.6 seconds, or 26 seconds).

Once the control parameters have been validly programmed, then a first step of the Auto-Set sequence (block 164) is to program the Auto-Set parameters. The operator is asked to enter a Maximum Sensor Rate for the Auto-Set sequence; but the other control parameters used during the Auto-Set sequence are set automatically to predetermined values. (Note, the Base Rate is not readjusted during the Auto-Set sequence because a change in the Base Rate causes auto-programming of other pacemaker parameters, such as the Max Track Rate, the Ventricular Refractory period, and the Atrial Refractory period.) The predetermined values of the Auto-Set control parameters are as follows: (1) the Sensor is programmed to PASSIVE; (2) the SIR Histogram Sampling Rate is programmed to EVERY EVENT (which is not a user-programmable value); (3) the Slope is programmed to "6" (which slope value is selected as the most optimum value for the Auto-Set sequence as it gives unique rates to 29 out of 32 sensor indexes along its curve); (4) the MSR is programmed to the highest user-programmable value (necessary in order to generate the maximum number of sensor indexes for the Desired Work Rates), while the MSR selected by the operator is used as the highest cut-off value for the applicable Desired Rates presented during the Auto-Set sequence; (5) the Reaction time is programmed to a hexadecimal value of $0 \times 11$, selected to ensure that the Reaction Time responds one step at a time along all valid points of a Slope of 6 for a maximum of 32 steps (Note, this Reaction time value does not correspond to any displayable Reaction Time values for a Slope of 6); (6) the Recovery Time is programmed to a hexadecimal value of $0 \times 9$, corresponding to a displayable setting of MEDIUM for a Slope of 6 (selected as a reasonable Recovery Time value for a Slope of 6).

After the Auto-Set parameters are set as described above (block 164), the patient is instructed to perform a specified exercise for a prescribed period of time, e.g, one minute. The type of exercise selected is chosen such that the physiological stress level associated with the exercise is considered as a NORMAL work level. While the exercise is performed, the SIR Histogram data is collected. During this time, as indicated above, the Sensor may be programmed to PASSIVE.

After the patient performs the Exercise at the NORMAL work level (block 166), the SIR Histogram Data collected during the Exercise is retrieved and examined (block 168). The Examination of the SIR Histogram Data looks for the Histogram Bin, designated as $B_N$, having at least five counts of the highest rate achieved (block 170). If the highest frequency rate Bin containing at least five counts corresponds to the highest user-programmable Max Sensor Rate, then that indicates the Threshold setting is too sensitive, i.e., too low (block 172). Similarly, if the total number of sampling counts contained in the range of Sensor Histogram bins extending from the bin with the lowest rate to the bin corresponding to the currently programmed Base Rate is less than two, then that also indicates a Threshold setting that is too sensitive. In either event, the Threshold is adjusted (block 174) so that it is not as sensitive and the SIR Histogram data is collected again after clearing the old Histogram data.

If the Threshold is not too sensitive (block 172), then an average rate $R_N$ associated with the Bin $B_N$ is computed (block 176). Such average rate is computed to be the mid-point between the Bin's low frequency and high frequency. Thus, if Bin 4, having a rate range of 83 to 90 ppm is determined to be $B_N$ (the bin of the highest frequency range having at least five counts), then the average rate $R_N$ is computed to be the mid-point between 83 and 90 ppm, or 86.5 ppm.

Once the average rate $R_N$ is determined, a Delta Rate, $R_\Delta$, is next computed. In accordance with one embodiment, the Delta Rate is computed as simply the difference between the average rate and the Base Rate (block 178), or $$R_\Delta = R_N - R_0.$$

With respect to FIG. 3, the Delta Rate in accordance with this embodiment is thus the relative SIR rate indicated on the vertical axis. In accordance with another embodiment, a Delta Rate for the Normal Work rate is computed as a function of the sensor index determined as described below and the pre-Auto-Set Slope setting, as described in Appendix B.

A corresponding sensor index $i_\Delta$ is next determined that corresponds to the Delta rate, $R_\Delta$, for the Auto-Set Slope Curve (Slope 6) (block 180). Thus, for example, if the Delta rate $R_\Delta$ is determined to be 20, then from FIG. 3 it is seen that the corresponding sensor index $i_\Delta$ is 8.

The average rate $R_N$ may also be considered as the Normal work rate because it is the average rate associated with the NORMAL exercise level performed at 66. Once $R_N$ is known, a determination is made as to whether the Threshold is too insensitive. The currently programmed Threshold is too insensitive if the Normal Work Rate $R_N$ is equal to the Base Rate. Said another way, the currently programmed Threshold is too insensitive if $R_\Delta$ is equal to 0. Thus, if $R_{66}=0$ (block then that indicates the Threshold is too insensitive (block 182), i.e., too high, and the Threshold is adjusted accordingly (block 174), and the SIR Histogram Data is obtained again after clearing the old SIR Histogram data. Using the sensor index $i_\Delta$, a determination is then made as to a corresponding SIR value, $SIR_i$, for each defined Slope curve (block 183) at the sensor index $i_\Delta$. Using the family of Slope curves shown in FIG. 3, for example, and assuming a Delta sensor index $i_\Delta$ of 8, it is seen that the relative values of SIR for each Slope curve, and the corresponding values of SIR (assuming an of 60 ppm) would be as shown in Table 1.

TABLE 1

| Slope Curve | Relative SIR$_i$ (ppm) | SIR$_i$ (ppm) |
|---|---|---|
| 1 | 8 | 68 |
| 2 | 10 | 70 |
| 3 | 12.5 | 72.5 |
| 4 | 15 | 75 |
| 5 | 18 | 78 |
| 6 | 20 | 80 |

TABLE 1-continued

| Slope Curve | Relative SIR$_i$ (ppm) | SIR$_i$ (ppm) |
|---|---|---|
| 7 | 23 | 83 |
| 8 | 27 | 87 |
| 9 | 32.5 | 92.5 |
| 10 | 37 | 97 |
| 11 | 46 | 106 |
| 12 | 53 | 113 |
| 13 | 62.5 | 122.5 |
| 14 | 75 | 135 |
| 15 | 92.5 | 152.5 |
| 16 | — | — |

A list of the SIR$_i$ values obtained from Table 1, or an equivalent list, is next displayed (block 184). From this displayed list, the operator selects a Desired SIR for the particular patient and Exercise level that was performed (block 186). In other words, the operator picks a NORMAL work rate that he would want (or expect) the patient to achieve at the Exercise level that was performed. For example, assuming the same conditions that apply to Table 1 above, the operator may determine that the patient should have desirably achieved a SIR of 87 given the Exercise level that was performed, thereby forcing a pacing rate of at least 87 ppm. In such case, the operator would select 87 from the list of possible SIR values at the NORMAL work level as the Desired SIR value (block 186). The Auto-Set routine then works backwards from the selected Desired SIR value to determine the corresponding Slope curve from which the desired SIR value was obtained. A corresponding set of sensor control parameters associated with the Slope curve thus determined is next defined (block 188). Such other parameters are generally as previously programmed, or as are reasonable for the selected Slope curve. (For example, the Base Rate and MSR would be as previously programmed.) The suggested Threshold would be the Threshold determined from the Auto-Set Routine that is neither too sensitive nor too insensitive. The Slope curve would be the Slope that gives the Desired SIR at the Delta index $i_\Delta$. The Reaction and Recovery Times would be reasonable values (e.g., MEDIUM) for the proposed Slope.) For the example in Table 1, assuming a Desired SIR value of 87, the Slope curve is 8. This selected Slope curve, and related sensor operating parameters are next displayed to the operator as a proposed set of sensor operating parameters (block 190). The operator is then given the option of programming the proposed set of operating parameters into the pacemaker (block 192). If the operator elects to program the proposed set of sensor control parameters into the pacemaker, then such values are programmed into the pacemaker (block 194), the SIR Histogram Data is cleared, and (if desired) the newly programmed parameters are again displayed (and optionally printed) (block 198). If the operator elects not to program the proposed set of sensor control parameters into the pacemaker, then the previous (pre-Auto-Set) sensor control parameter set is programmed back into the pacemaker (block 196), the SIR Histogram data is cleared, the programmed parameters are displayed (block 198), and the Auto-Set routine is concluded.

Figure 8:
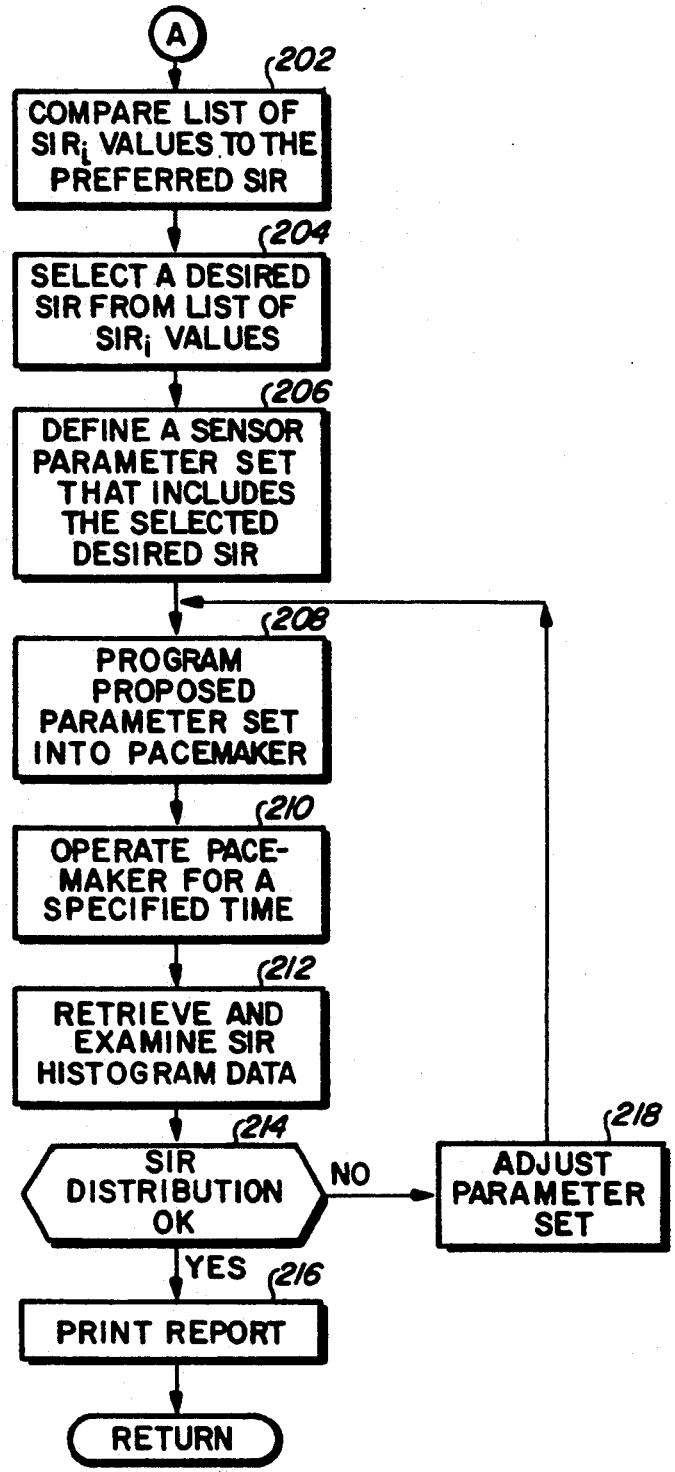
FIG. 8 shows a variation of the flowchart of FIG. 7 used to automatically select a desired SIR and program a set of sensor parameters that generate the SIR in the pacemaker.

FIG. 8 shows an alternative embodiment of the Auto-Set routine used to automatically select a desired SIR and program a set of corresponding sensor parameters in the pacemaker. FIG. 8 is intended to replace FIG. 7, and the combination of FIGS. 6 and 8 thus represents the flowchart of the alternative embodiment of the Auto-Set routine. In accordance with such alternative embodiment, when the preliminary programming or interrogating is done (at block 160) of the sensor control parameters, a Preferred SIR for the anticipated exercise that will be done, and/or a Preferred Histogram Distribution, is also entered. Then, when the list of possible SIR, values is determined at the sensor index $i_\Delta$ (block 183, FIG. 6), such list is automatically compared to the Preferred SIR previously entered (block 202, FIG. 8). Based on such comparison, one of the possible $SIR_i$ values is selected as the Desired SIR value (block 204). Such selection is made based on the SIR value that is closest to the Preferred SIR value. If two values are equally close, then appropriate tie-breaking rules are imposed to make the selection.

After the Desired SIR has been selected, a corresponding set of sensor control parameters that includes the Slope curve that produced the Desired SIR is defined (block 206). Such set of sensor control parameters is then programmed into the pacemaker (block 208), and the SIR Histogram data is cleared. The pacemaker then operates for a specified time using the newly programmed sensor control parameters (block 210), while collecting new SIR Histogram and other data. After the specified time, such SIR Histogram data is retrieved and examined (block 212). Based on such examination (block 214), the parameter set may be adjusted as required in order to produce the preferred SIR Distribution (block 218). A report of the examination may also be printed (block 216). Thus, the Auto-Set routine in accordance with this embodiment of the invention automatically determines and programs a set of operating parameters into the pacemaker, and adjusts such operating parameters over time, as required, in order to force a preferred SIR Histogram distribution.

It is noted that at any step of the Auto-Set sequence, the operator may cancel the routine. When a cancel request is made, the operator is prompted to confirm the cancellation. Once confirmed, all of the sensor control parameters are returned to their pre-Auto-Set values. If the original Sampling Rate was unknown or invalid, it is programmed to a default value of 1.6 seconds.

Figure 9:
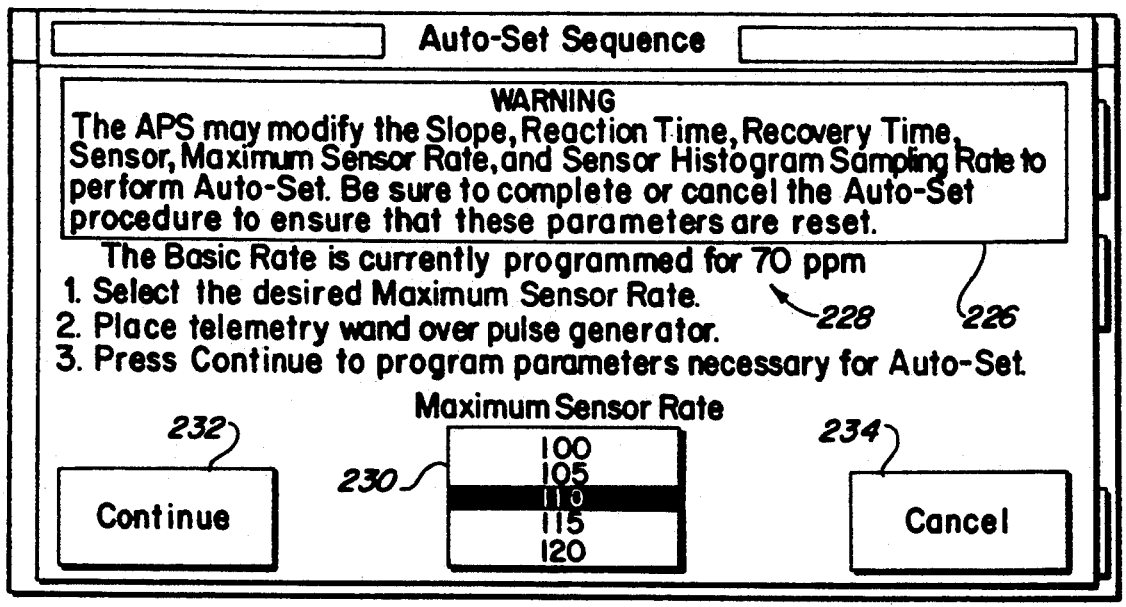
FIGS. 9, 10, and 12 are various screen displays that are displayed while carrying out the Auto-Set method of FIGS. 6 and 7, which screen displays provide instructions to the physician and patient, allow the physician to make a preferred rate selection, and display the preferred set of sensor parameters determined by the Auto-Set method.
Figure 10:
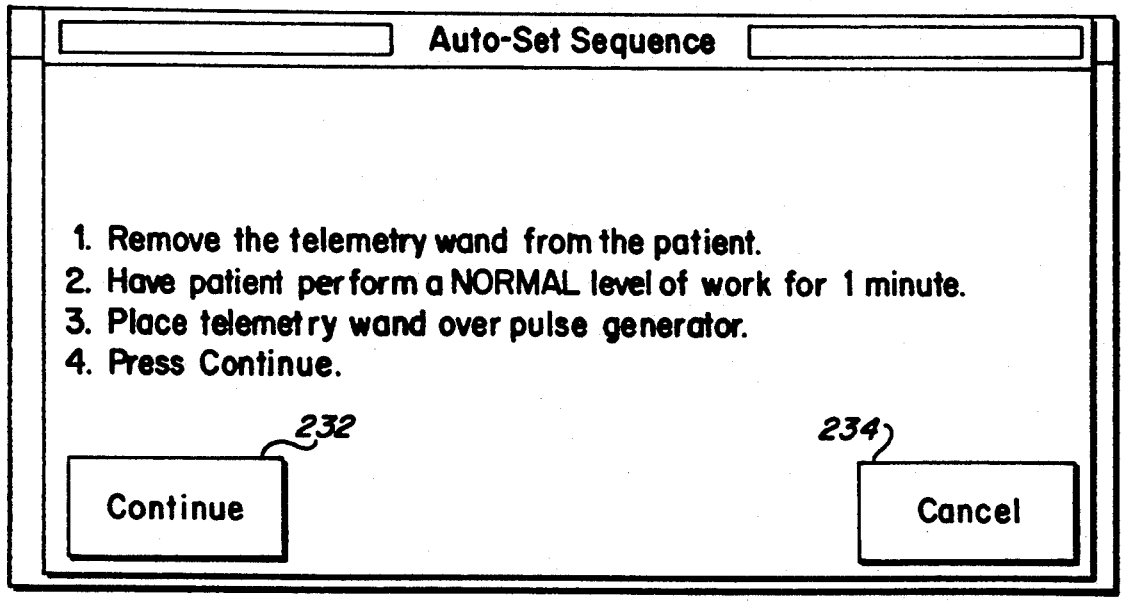
Figure 12:
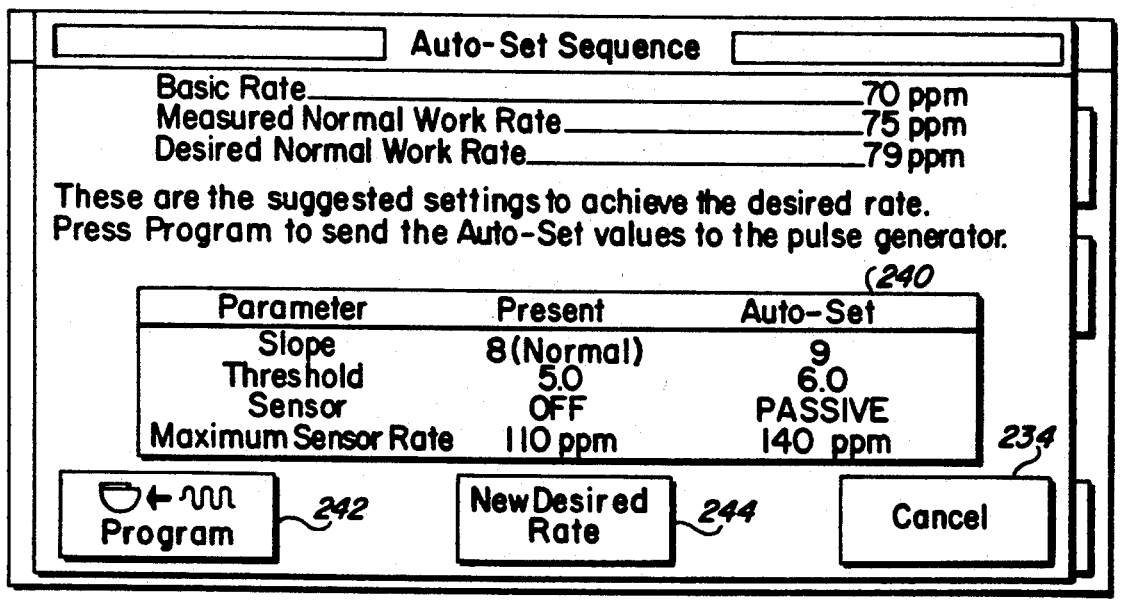

Referring next to FIGS. 9, 10, and 12, there are shown the main screen displays that are displayed by the APS-II/MTM external programmer while carrying out the Auto-Set routine. In general, the screen displays provide instructions to the operator, allow the operator to make a preferred rate selection, and display the preferred set of sensor parameters determined by the Auto-Set sequence.

FIG. 9, for example, shows the first screen displayed when the Auto-Set sequence is invoked. The screen shown in FIG. 9 is available from either the "Sensor Parameters" pop-up menu or the Programmed Data Display Options pop-up menu available on the APS-II/MTM programmer. As indicated, the first screen warns the operator with a warning message 226 that many of the sensor control parameters may be modified by the Auto-Set routine, and that it is important the Auto-Set routine be completed or canceled so that any of the sensor control parameters that are changed can be reset. The screen also indicates the current value of the Base Rate (shown as the Basic Rate) at area 228. The operator is further requested in the first screen to select the desired Maximum Sensor Rate. Such selection is done by way of a thumbwheel icon 230 that displays a list of possible MSR values. By simply touching the icon 230 at the desired value, either above or below the current selected value, a new value is selected and highlighted. (This is accomplished by way of a touch sensitive screen that overlays the display screen on which the screen is displayed.) The operator is further instructed to place the telemetry wand over the pulse generator and to press "Continue" if the Auto-Set sequence is to be carried out. The screen displays a "Continue" icon button 232, and a "Cancel" icon button 234, which may be pressed (touched) in order to continue or cancel the Auto-set sequence.

Upon pressing the Continue button 232 in the first screen, the control parameters necessary to carry out the Auto-Set sequence are programmed into the pacemaker as described above. If such Auto-Set programming is successful, then a second screen is displayed as shown in FIG. 10. (If such Auto-Set programming is not successful, then the operator is prompted with appropriate error messages to reprogram, e.g., by pressing the Continue button again, or equivalent error-recovery steps.) As seen in FIG. 10, this second screen instructs the operator to remove the telemetry wand from the patient, and to have the patient perform a NORMAL level of work for 1 minute. After such NORMAL level of work, the operator is instructed to replace the telemetry wand over the pacemaker and press the Continue button 232. During the NORMAL level of work, the SIR Histogram data is accumulated in the pacemaker on an EVERY EVENT sample basis with the pacemaker operating in a Sensor PASSIVE mode. Upon pressing the Continue button, such SIR Histogram data is retrieved from the pacemaker and examined as described above in conjunction with FIGS. 6 and 7.

If after examination of the SIR Histogram data, it is not possible to determine a stable work rate (as might occur, for example, if none of the Histogram bins contain at least three counts), then an error message is displayed over the second screen indicating the "The activity performed did not result in a stable work rate." The patient is then required to repeat the exercise.

If after an examination of the SIR Histogram data a determination is made that the SIR response was too sensitive, i.e., that the Threshold is set too low, then a intermediate screen is displayed that guides the operator through a resetting of the Threshold so that it is less sensitive.

Similarly, if after an examination of the SIR Histogram data a determination is made that the SIR response was too insensitive, i.e., that the Threshold is set too high, then another intermediate screen is displayed that guides the operator through a resetting of the Threshold so that it is more sensitive.

Figure 11:
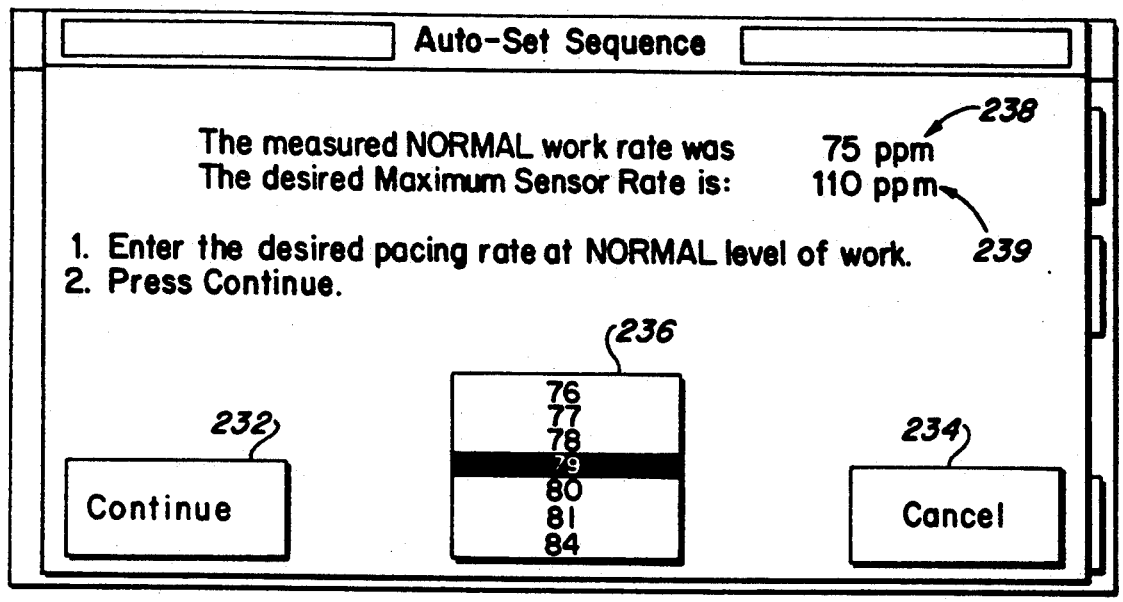

If after an examination of the SIR Histogram data a stable work rate is ascertainable, then a third screen is displayed as shown in FIG. 11. As described in conjunction with FIG. 6 above, assuming a proper Threshold setting, the examination of the SIR Histogram data allows a NORMAL work rate to be determined. Such NORMAL work rate is displayed on the third screen, as shown at 238. The third screen also shows the Maximum Sensor Rate (MSR) that was selected during the display of the first Auto-Set screen (FIG. 9) at 239. The third screen further requests that the operator select the desired pacing rate at the NORMAL level of work. To make this selection, a thumbwheel icon 236 is displayed that lists the $SIR_i$ values corresponding to the various Slope curves at the Delta sensor index value $i_\Delta$, as described previously.

Once the operator has made the selection of the Desired pacing rate, the Continue button 232 is again pressed. Pressing the Continue button 232 at the third screen causes a fourth Auto-Set screen to be displayed as shown in FIG. 12. The fourth screen shows the Base Rate, the measured Normal Work Rate, and the Desired Normal Work Rate (as selected at the third screen). Based on the measured Normal Work Rate and the Desired Normal Work Rate, the Auto-Set sequence computes a suggested set of sensor control parameters. Such suggested set of sensor control parameters is displayed in a window 240 that is part of the fourth screen. Included in the window 240 are the "present" (pre-Auto-Set) values of the sensor control parameters.

If the operator approves of the proposed set of sensor control parameters, a Program button 242 on the fourth screen may be pressed, causing the Auto-Set values to be programmed in the rate-responsive pacemaker. If the operator would like to select another Desired pacing rate, then a "New Desired Rate" button 244 may be pressed, causing the third screen (FIG. 11) to again be displayed. At any time, if desired, the Cancel button 234 may be pressed to cancel the Auto-Set sequence. If the cancel button 232 is pressed, then a warning message pops up informing the operator that all parameters will be restored to the Pre-Auto-Set State, and requests for confirmation of the cancellation.

There are numerous ways and methods that may be used within the APS-II/MTM or equivalent external programmer in order to carry out the Auto-Set sequence routine as described above. In the preferred embodiment, a series of programs are included in the detachable program module of the APS-II/MTM that instruct the processor within the APS-II/MTM to carry out the Auto-Set routine substantially as described above in conjunction with FIGS. 6 and 7, and FIGS. 9–12. Appendix A, attached hereto, is a Summary Table that lists the programs and routines, and their respective functions, inputs and outputs, used within the APS-II/MTM in order to carry out the Auto-Set sequence in accordance with the best mode of the invention. It is submitted that those skilled in the programming arts, given the description of the Auto-Set sequence presented herein, could readily fashion appropriate routines and programs that could carry out the Auto-Set function; and that such persons of skill in the art could also readily ascertain, from the summary descriptions presented in Appendix A, the best mode of carrying out the invention.

Appendix B, likewise attached hereto, shows an Auto-Set Delta Rate algorithm that may be used in accordance with one embodiment of the Auto-Set method of the invention. Appendix C, also attached hereto, is a Table used by the Auto-Set Delta Rate algorithm shown in Appendix B.

As described above, it is thus seen that the present invention significantly simplifies the way in which the sensor parameters of a rate-responsive pacemaker are set, and that removes much of the guess work that has previously accompanied such task.

As further described above, it is seen that a programming tool or aid is provided by the invention for use by a physician, or other medical personnel, to accurately predict the expected behavior of an implanted rate-responsive pacemaker with a given programmed state, and that facilitates the programming of the pacemaker in such state. Significantly, the invention allows the sensor parameters of a rate-responsive pacemaker to be set or programmed based on what the physician wants to see happen for a particular patient, i.e., that sets the sensor control parameters to provide a given sensor indicated rate signal for a well-defined level of exercise, or load placed on the patient's heart.

Several variations of the invention as described above are also possible. For example, one such variation contemplates the use of the Event Record, described in one of the copending patent applications cited above, to store pacing events in sequence as such events occur while the patient is performing the exercise specified by the Auto-Set sequence. By storing the pacing event data during the patient exercise period, the Event Record may thus be used as an alternate to the SIR Histogram. Moreover, with the additional time component available in the Event Record, an extension of the recommendations provided by Auto-Set is possible. That is, in addition to recommending rate values at the end of the exercise, a graph may be generated that represents the expected response of the patient to exercise with the newly selected Slope, using the data collected during the actual exercise period as a baseline. The entire set of such graphs, under all valid slope values, may then be used to calculate a theoretical work envelope, which work envelope may be used to better predict the patient/pacemaker response.

Alternatively, the raw sensor data may be stored in the Event Record during the Auto-Set exercise period. Such data, when examined, would thus allow the operator to propose changing the sensor parameters in a way that makes maximum use of the raw sensor data, including the generating of graphs that depict the expected pacemaker behavior verses time.

Still further, and as indicated previously, the present invention is not limited to a single physiological sensor. Rather, multiple sensors may be employed, and the Auto-Set routine can provide valuable information concerning the operation and use of all such multiple sensors.

Moreover, as also suggested above in connection with FIG. 8, it is contemplated that the pacemaker could continuously monitor the SIR Histogram data and make automatic adjustments to the Slope, Threshold and other sensor parameters to make the SIR Histogram statistics match a desired distribution. As disclosed above in conjunction with FIG. 8, such automatic adjustments could be made periodically when the programmer is coupled to the pacemaker. Alternatively, by programming the Auto-Set steps and features into the pacemaker itself, including a desired SIR Histogram distribution, such automatic adjustment could occur within the pacemaker on a recurring basis without any control from an external programmer.

While the invention herein disclosed has been described by means of specific embodiments and applications thereof, numerous modifications and variations could be made thereto by those skilled in the art without departing from the scope of the invention set forth in the claims.

APPENDIX A

Summary of Programming Logic Routines That Support Auto-Set

1.
```
/*|-------------------------------------------------*/
GLOBAL COUNT syn_as_init(mrate_ix)
/*-------------------------------------------------*/
NAME
    syn_as_init - autoset initialization.
AUTHOR FUNCTION
    Program sensor parameters to values which will gives optimal
    Auto-Set results.
INPUTS
    mrate_ix - Max Sensor Rate right value index.
RETURNS
    COILISOUT      - Telemetry head is unplugged.
    INCOMPLETE     - Programming/interrogating was unsuccessful.
    SUCCESSORA_BADRP - Synchrony portion of pacer isn't responding.

MDLDIFFERS     - Pacer has changed.
    OKSAMEPACER    - Operation successful; Pacer hasn't changed.
    PUTMAGIN       - Function requires telemetry magnet inserted.
    REMOVEMAG      - Function requires telemetry magnet removed.
```

2.
```
/*|-------------------------------------------------*/
GLOBAL BOOL syn_as_rechk()
/*-------------------------------------------------*/
NAME
    syn_as_rechk - re-check parameters settings
AUTHOR FUNCTION
    Check if this pacer has been programmed differently to accomodate
    Auto-Set?
INPUTS
    None.
RETURNS
    YES    The pacer requires programming to return to its original state
    NO     The pacer has not been changed.
```

3.
```
/*|-------------------------------------------------*/
GLOBAL COUNT syn_as_reset()
/*-------------------------------------------------*/
NAME
    syn_as_reset - reset parameters to pre autoset values
AUTHOR FUNCTION
    Reset the Pacer back to its pre-Auto-Set values.
INPUTS
    None
RETURNS
    COILISOUT      - Telemetry head is unplugged.
    INCOMPLETE     - Programming/interrogating was unsuccessful.
    MDLDIFFERS     - Pacer has changed.
    OKSAMEPACER    - Operation successful; Pacer hasn't changed.
    PUTMAGIN       - Function requires telemetry magnet inserted.
    REMOVEMAG      - Function requires telemetry magnet removed.
    ASFAIL         - Auto-Set can not proceed, batch store fails.
```

4.
```
/*|-------------------------------------------------*/
GLOBAL COUNT syn_as_nmwrk(text_buf)
/*-------------------------------------------------*/
NAME
    syn_as_nmwrk - autoset normal work rate
AUTHOR FUNCTION
    Read the sensor histogram counters to compute the normal work rate.
    If the total number of sampling counts is less than 30, or no bin
    has a count of at least 5, then return message code to get the
    patient to repeat the exercise.
    If the normal work computed greater than the highest user programmable
    max sensor rate, its value shall be default to the highest user
    programmable Max Sensor Rate.
```

```
        If the total sampling counts from the bin with the lowest sampling rate
        to the bin associated with the base rate is <= 1, this indicates that
        the current Threshold setting is too sensitive.
        If the normal work rate equals to the basic rate, return
        the message code to have the user program Threshold
        to a more sensitive (lower) value.
        If the normal work is valid, then convert the value to text string
        in the buffer passed in to this routine.
    INPUTS
        text_buf    - Buffer for the computed Normal Work values.

RETURNS
        COILISOUT   - Telemetry head is unplugged.
        INCOMPLETE  - Programming/interrogating was unsuccessful.
        MDLDIFFERS  - Pacer has changed.
        OKSAMEPACER - Operation successful; Pacer hasn't changed.
        PUTMAGIN    - Function requires telemetry magnet inserted.
        REMOVEMAG   - Function requires telemetry magnet removed.
        ASPRGLOWTHR - Program Threshold to a lower setting.
        ASPRGHIGHTHR - Program Threshold to ahigher setting.
        ASRMVWAND   - Remove telemetry wand from pacer for 1 minute.
        ASREPEATEXR - Patient is required to repeat the exercise routine.

/*|-----------------------------------------------------------------*/
    GLOBAL COUNT syn_as_nwtbw(vals_buf, tbw_cnt, cur_idx)
    /*-------------------------------------------------------------------
    NAME
        syn_as_nwtbw - normal work rate thumbwheel values
    AUTHOR FUNCTION
        Determine the desired work rates that should be placed into
        the NORMAL work rate thumbwheel.
    INPUTS
        vals_buf    - Buffer for the computed thumbwheel values.
        tbw_cnt     - Number of displayable thumbwheel values computed.
        cur_idx     - Current slope right index
    RETURNS
        OKSAMEPACER - Thumbwheel selectable values has at least 1 setting.
        ASFAIL      - Auto-Set fails, thumbwheel is empty.

/*|-----------------------------------------------------------------*/
    GLOBAL COUNT syn_as_batent(norm_wrk_index)
    /*-------------------------------------------------------------------
    NAME
        syn_as_batent - batch enter parameters
    AUTHOR FUNCTION
        Batch store the auto-set suggested values of all
        parameters whose values are required to be re-programmed as a
        result of the autoset sequence.
    INPUTS
        norm_wrk_index - Thumbwheel index for the Normal Work Rate.
    RETURNS
        ASBATCHOK   - Autoset batch stored okay.
        ASFAIL      - Auto-set cannot proceed because
                      batch store fails.
        ...

/*|-----------------------------------------------------------------*/
    LOCAL COUNT syn_as_pre_prog()
    /*-------------------------------------------------------------------
    NAME
        syn_as_pre_prog - pre autoset programming
    AUTHOR FUNCTION
        Program parameters to settings for optimal autoset results.
        Program Slope setting to 6. Also program SLMORG and SLMMAX to values
        corresponding to the Slope setting.
        Program Sensor to PASSIVE.
        Program Max Sensor Rate to the highest user programmable setting.
        Program sensor histogram sampling rate to Per Event.
        All above parameters are batched store first then call pl_prg()
        to do the programming at once.
    INPUTS
        None
    RETURNS
        COILISOUT   - Telemetry head is unplugged.
        INCOMPLETE  - Programming/interrogating was unsuccessful.
        MDLDIFFERS  - Pacer has changed.
```

```
             OKSAMEPACER - Operation successful; Pacer hasn't changed.
             PUTMAGIN    - Function requires telemetry magnet inserted.
             REMOVEMAG   - Function requires telemetry magnet removed.
```

8.
```
        /*|-------------------------------------------------------*/
        LOCAL VOID syn_bld_desrate(maxidx)
        /*---------------------------------------------------------
        NAME
            syn_bld_desrate - build desired work rate
        AUTHOR FUNCTION
            Build the desired rates of all applicable slopes at sensor
            index of maxidx.
        INPUTS
            maxidx   - Highest sensor index.
        RETURNS
            None.
```

9.
```
        /*|-------------------------------------------------------*/
        LOCAL VOID syn_bld_slope(cur_slope, max_entry, curve_tab)
        /*---------------------------------------------------------
        NAME
            syn_bld_slope - build slope curve
        AUTHOR FUNCTION
            Build the curve of the slope index passed in to this routine as an argument.
            Each Slope has eight rate step deltas (RATESTP), each rate step delta
            is made up of a low and a high nibble. Refer to the Auto-set programming
            logic specification (ES0807) for the detailed algorithm to build
            the slope curve.
        INPUTS
            cur_slope    - Currently process Slope index.
            max_entry    - Highest sensor index.
            curve_tab    - Buffer to store the computed values of each sensor index.
        RETURNS
            None.
```

10.
```
        /*|-------------------------------------------------------*/
        GLOBAL COUNT syn_as_thrtbw(tbw_range, vals_buf, tbw_cnt, def_idx)
        /*---------------------------------------------------------
        NAME
            syn_as_thrtbw - autoset threshold thumbwheel values
        AUTHOR FUNCTION
            Build the selectable values of the threshold thumbwheel.
        INPUTS
            tbw_range   - Applicable range of thumbwheel values.
            vals_buf    - Buffer to store the computed displayable values.
            tbw_cnt     - Number of displayable values in the thumbwheel.
        RETURNS
            OKSAMEPACER - All okay.
            ASFAIL      - Auto-Set can not proceed, thumbwheel has no value.
            ASMAXTHR    - Hit the maximum Threshold setting.
```

11.
```
        /*|-------------------------------------------------------*/
        GLOBAL COUNT syn_as_prgthr(thr_tbw_idx, prg_flg)
        /*---------------------------------------------------------
        NAME
            syn_as_prgthr - autoset program threshold
        AUTHOR FUNCTION
            Program the selected threshold setting to the pacer.
        INPUTS
            thr_tbw_idx - Thumbwheel index for the threshold parameter.
        RETURNS
            COILISOUT   - Telemetry head is unplugged.
            INCOMPLETE  - Programming/interrogating was unsuccessful.

MDLDIFFERS  - Pacer has changed.
            OKSAMEPACER - Operation successful; Pacer hasn't changed.
            PUTMAGIN    - Function requires telemetry magnet inserted.
            REMOVEMAG   - Function requires telemetry magnet removed.
            ASFAIL      - Auto-Set fails to proceed, batch enter failed.
```

```
/*|-------------------------------------------------------------*/
LOCAL COUNT syn_hi_msr(xcode)
/*---------------------------------------------------------------
NAME
    syn_hi_msr - highest user programmable Maximum Sensor Rate xcode
AUTHOR FUNCTION
    This function retrieve the xcode of the highest user programmable
    max sensor rate.
INPUTS
    xcode     - Highest user programmable Max Sensor Rate xcode
RETURNS
    Highest user programmable Max Sensor Rate display value /*|-------------------------------------------------------------*/
GLOBAL COUNT syn_as_prechk()
/*---------------------------------------------------------------
NAME
    syn_as_prechk - preliminary autoset sensor parameters validity check.
AUTHOR FUNCTION
    Check if parameters required for autoset have valid values. If
    unknown value detected during the first loop of autoset, then return
    flag to have the pacer re-interrogated. Otherwise, return message
    code to have the user re-programmed the unknown parameter.
    If all parameters required for autoset are valid, then return
    OKSAMEPACER.
INPUTS None.
RETURNS
    OKSAMEPACER      - Operation successful; No unknown parameters
    ASPRGRAT         - Program Base Rate First
    ASPRGSNR         - Program Sensor First
    ASPRGTHR         - Program Threshold First
    ASPRGSLP         - Program Slope First
    ASPRGMSR         - Program Max Sensor Rate First
    ASPRGRCT         - Program Reaction Time First
    ASPRGRCV         - Program Recovery Time First
    ASUNKNOWNVAL     - Unknown parameters values detected /*|-------------------------------------------------------------*/
LOCAL UTINY syn_masidx(tbw_range)
/*---------------------------------------------------------------
NAME
    syn_masidx - Measured Average Sensor right index for auto-set sequence.
AUTHOR

FUNCTION

It retrieves the current Measured Average Sensor index,
    and divide it by 10 as to map the value to values in
    the Threshold thumbwheel.
INPUTS
    tbw_range - Expected range of the Threshold thumbwheel values
RETURNS
    mas_idx - Measured Average Sensor right index.

/*|-------------------------------------------------------------*/
LOCAL COUNT syn_thr_range(tbw_range, min_idx, max_idx, cur_thr_idx, brk_index)
/*---------------------------------------------------------------
NAME
    syn_thr_range - Applicable range of Threshold thumbwheel values
AUTHOR FUNCTION
    This routine determines the minimum and the maximum applicable
    Threshold values for its thumbwheel.
INPUTS
    tbw_range    - Threshold values expected: either higher or lower than
                   the currently programmed value.
    min_idx      - Pointer to the minimum applicable index.
    max_idx      - Pointer to the maximum applicable index
    brk_index    - Flag to indicate if any interval in the applicable range
                   of indexes.
RETURNS
    OKSAMEPACER - Everything okay.
    ASMAXTHR    - Hit the maximum Threshold value
```

12.

13.

14.

15.

```
/*|---------------------------------------------------*/
LOCAL VOID syn_thr_txt(min_idx, max_idx, num, thrbits)
/*---------------------------------------------------*/
NAME
    syn_thr_txt - Threshold value in text format
AUTHOR FUNCTION
    This routine process each bit of the Threshold bitmap, if the bit
    is set for the index, call syn_thr_ele() to pad the element into
    text format.
INPUTS
    min_idx    - Minimum applicable index.
    max_idx    - Maximum applicable index
    num        - Number of applicable values in the thumbwheel
    thrbits    - Bitmap indicating if the bit is set.
RETURNS
    None.

/*|---------------------------------------------------*/
LOCAL VOID syn_thr_ele(thridx, num)
/*---------------------------------------------------*/
NAME
    syn_thr_ele - Pad the Threshold element to text string
AUTHOR FUNCTION
    This routine pads the Threshold value into thumbwheel string.
INPUTS
    thridx  - Processing bit
    num     - Counter of the applicable values
RETURNS /*|---------------------------------------------------*/
LOCAL  COUNT syn_as_prg(srate)
/*---------------------------------------------------*/
NAME
    syn_as_prg
AUTHOR FUNCTION
    Batch store the sensor histogram new sampling rate and the reset bit.
    Call pl_prg() to program the batch store values to the pacer.
INPUT
    srate - sampling rate index
RETURNS
    return values from pl_prg()
```

APPENDIX B

Auto-Set Delta Rate Algorithm

Delta Rate is a function of Slope and Sensor index.
Sensor index ranges from 0 to 31 (0 is the lowest and 31 is the highest). It is denoted as i in the following equations.
Applicable Slope values range from 1 (Least Responsive) to 16 (Most Responsive). It is denoted by $Slope_k$.

If i is an even number, then $j = \frac{i}{2}$ then

If j is an even number, then $m = \frac{j}{2}$ and $$\text{Delta Rate}[i] = \sum_{n=1}^{n=m} (\text{Ratestep}[n] \text{ of } Slope_k) \cdot 2.5$$

If j is an odd number, then $m = \frac{j-1}{2}$ and $$\text{Delta Rate}[i] = \sum_{n=1}^{n=m} (\text{Ratestep}[n] \text{ of } Slope_k) \cdot 2.5 +$$

(low nibble of Ratestep[m + 1] of $Slope_k \cdot 2.5$)

If i is an odd number, then $$\text{Delta Rate}[i] = \frac{\text{Delta Rate}[i-1] + \text{Delta Rate}[i+1]}{2}$$

Refer to Appendix C for values of Ratestep[n].

APPENDIX C
Slope Values and Codes

| Value | SLOPE | SSENS | RATE STP 1 | RATE STP 2 | RATE STP 3 | RATE STP 4 | RATE STP 5 | RATE STP 6 | RATE STP 7 | RATE STP 8 |
|---|---|---|---|---|---|---|---|---|---|---|
| 1 (Least Resp) | 0 × 0 | 1 | 0 × 10 | 0 × 11 | 0 × 10 | 0 × 11 | 0 × 10 | 0 × 00 | 0 × 01 | 0 × 00 |
| 2 | 0 × 1 | 1 | 0 × 11 | 0 × 11 | 0 × 11 | 0 × 11 | 0 × 11 | 0 × 01 | 0 × 01 | 0 × 00 |
| 3 | 0 × 2 | 1 | 0 × 21 | 0 × 11 | 0 × 21 | 0 × 11 | 0 × 12 | 0 × 11 | 0 × 10 | 0 × 00 |
| 4 | 0 × 3 | 1 | 0 × 22 | 0 × 11 | 0 × 21 | 0 × 12 | 0 × 12 | 0 × 11 | 0 × 11 | 0 × 01 |
| 5 | 0 × 4 | 1 | 0 × 22 | 0 × 12 | 0 × 22 | 0 × 12 | 0 × 22 | 0 × 12 | 0 × 11 | 0 × 01 |
| 6 | 0 × 5 | 1 | 0 × 22 | 0 × 22 | 0 × 22 | 0 × 22 | 0 × 22 | 0 × 22 | 0 × 21 | 0 × 01 |
| 7 | 0 × 6 | 1 | 0 × 23 | 0 × 22 | 0 × 23 | 0 × 23 | 0 × 22 | 0 × 12 | 0 × 22 | 0 × 02 |
| 8 (Normal) | 0 × 7 | 1 | 0 × 33 | 0 × 32 | 0 × 33 | 0 × 23 | 0 × 22 | 0 × 22 | 0 × 22 | 0 × 02 |
| 9 | 0 × 8 | 1 | 0 × 43 | 0 × 33 | 0 × 43 | 0 × 33 | 0 × 32 | 0 × 22 | 0 × 22 | 0 × 11 |
| 10 | 0 × 9 | 1 | 0 × 44 | 0 × 34 | 0 × 44 | 0 × 34 | 0 × 34 | 0 × 22 | 0 × 22 | 0 × 11 |
| 11 | 0 × A | 1 | 0 × 45 | 0 × 45 | 0 × 45 | 0 × 45 | 0 × 33 | 0 × 23 | 0 × 22 | 0 × 01 |
| 12 | 0 × B | 1 | 0 × 65 | 0 × 55 | 0 × 56 | 0 × 45 | 0 × 34 | 0 × 13 | 0 × 00 | 0 × 00 |
| 13 | 0 × C | 1 | 0 × 66 | 0 × 67 | 0 × 67 | 0 × 55 | 0 × 05 | 0 × 00 | 0 × 00 | 0 × 00 |
| 14 | 0 × D | 1 | 0 × 87 | 0 × 87 | 0 × 68 | 0 × 26 | 0 × 00 | 0 × 00 | 0 × 00 | 0 × 00 |
| 15 | 0 × E | 1 | 0 × 99 | 0 × 9A | 0 × 68 | 0 × 03 | 0 × 00 | 0 × 00 | 0 × 00 | 0 × 00 |
| 16 (Most Resp) | 0 × F | 1 | 0 × CC | 0 × AC | 0 × 07 | 0 × 00 | 0 × 00 | 0 × 00 | 0 × 00 | 0 × 00 |

What is claimed is:

1. A rate-responsive pacing system comprising:
   (1) an implantable rate-responsive pacemaker including:
      (a) sensing means for sensing natural contractions of a heart,
      (b) stimulation means for generating stimulation pulses for delivery to the heart at a prescribed pacing rate in the absence of sensed natural contractions,
      (c) physiological sensor means for sensing a physiological parameter and generating a sensor indicated rate (SIR) signal as a function thereof,
      (d) control means for defining said prescribed pacing rate as a selected one of either a programmed pacing rate value or said SIR signal, and
      (e) counting means for counting and storing each occurrence of said SIR signal that falls within one of a plurality of rate ranges, whereby SIR histogram data is collected within said rate-responsive pacemaker; and
   (2) an external programming device having:
      (a) telemetry means for establishing an RF telemetry link with said implantable pacemaker through which said SIR histogram data may be retrieved,
      (b) distinguishing means for identifying which of a plurality of different pacemaker models said implantable pacemaker is,
      (c) programming means for selected control data into said rate-responsive pacemaker through said RF telemetry link, said control data including said programmed value of said pacing rate, an indication of whether the programmed value or the SIR signal is to be used to define said pacing rate, and a set of SIR control parameters that define the manner in which said SIR signal is generated from the physiological parameter sensed by said physiological sensor means, and
      (d) processing means for processing said SIR histogram data so as to produce a recommended set of SIR control parameters for programming into said rate-responsive pacemaker.

2. The rate-responsive pacing system, as set forth in claim 1, wherein said physiological sensor means includes:
   a physiological sensor that generates a raw signal as a function of the sensed physiological parameter; and
   a rate-responsive sensor processing subsystem that processes said raw signal as directed by said SIR control parameters in order to produce said SIR signal, said SIR control parameters thereby defining the relationship between said raw signal and SIR signal.

3. The rate-responsive pacing system, as set forth in claim 2, wherein said SIR control parameters used by said rate-responsive sensor processing subsystem include a Threshold parameter and a Slope parameter, said Threshold parameter defining a threshold that said raw signal must exceed before said raw signal is considered significant, said Slope parameter defining a transfer function relationship between the amount of said raw signal that exceeds said threshold and said SIR signal.

4. The rate-responsive pacing system, as set forth in claim 3, wherein said SIR control parameters further include a Sensor control parameter that allows said rate-responsive sensor processing subsystem to be programmed to one of an ON, OFF, or PASSIVE mode; the ON mode of said rate-responsive sensor processing subsystem causing said subsystem to process said raw signal, generate said SIR signal therefrom, and deliver said SIR signal to said control means where it is used to define the prescribed pacing rate; the OFF mode of said rate-responsive sensor processing subsystem causing said subsystem to be turned off, whereby said control means uses said programmed pacing rate value to define said prescribed pacing rate; and the PASSIVE mode of said rate-responsive sensor processing subsystem causing said subsystem to process said raw signal, generate said SIR signal therefrom, but not deliver said SIR signal to said control means, whereby said control means uses said programmed pacing rate value to define said prescribed pacing rate.

5. The rate-responsive pacing system, as set forth in claim 4, wherein said PASSIVE mode of said rate-responsive sensor processing subsystem further allows said SIR signal to be counted and stored by said counting means, whereby the SIR histogram data is collected within said rate-responsive pacemaker even when said SIR signal is not used to define the prescribed pacing rate of the pacemaker.

6. The rate-responsive pacing system, as set forth in claim 5, wherein the programming means includes means for selectively initiating an Auto-Set sequence when said external programming device is in contact with said implantable rate-responsive pacemaker through said RF telemetry link, said Auto-Set sequence establishing a preferred Slope parameter for said rate-responsive sensor processing subsystem based on a desired pacing rate selected by an operator of said external programming device for a given exercise level.

7. The rate-responsive pacing system, as set forth in claim 6, wherein said Auto-Set sequence further establishes a Threshold parameter for said rate-responsive sensor processing subsystem that is not too sensitive nor too insensitive to the raw signal generated by said physiological sensor.

8. The rate-responsive pacing system, as set forth in claim 6, wherein said Auto-Set sequence includes:
means for setting the SIR control parameters within said rate-responsive pacemaker to known values, including programming said Sensor control parameter so that said rate-responsive sensor processing subsystem is programmed to its PASSIVE mode and so that SIR histogram data is collected during said PASSIVE mode; and
means for instructing a patient to perform a exercise for a prescribed time period.

9. The rate-responsive pacing system, as set forth in claim 8, wherein said processing means within said external programming device includes:
means for retrieving the SIR histogram data collected during the prescribed time period that the exercise was performed;
means for analyzing the retrieved SIR histogram data to determine a work rate;
means for generating a list of potential pacing rates that could have been provided during the period said exercise was performed as a function of the Slope parameter selected; and
means for selecting one of said potential pacing rates as a desired pacing rate during the prescribed time period that the exercise was performed, whereby a particular one of said Slope parameters is also selected as a preferred Slope parameter for use with said rate-responsive pacemaker.

10. An Auto-Set system for use within an external programming device in contact with an implantable rate-responsive pacemaker through an RF telemetry link,
said rate-responsive pacemaker having:
means for sensing natural cardiac activity,
means for generating stimulation pulses in the absence of sensed natural cardiac activity,
a sensor from which a sensor indicated rate (SIR) signal is derived in accordance with a prescribed relationship, said SIR signal being selectively utilized within said rate-responsive pacemaker to define the rate at which said rate-responsive pacemaker generates stimulation pulses in the absence of sensed natural cardiac activity, and
means for detecting and storing selected pacing events associated with the operation of said pacemaker, including a count of said SIR signals classified by rate;
said external programming device having:
means for establishing said RF telemetry link with said rate-responsive pacemaker,
mans for distinguishing means for identifying which of a plurality of different pacemaker models said rate-responsive pacemaker is; and
means for programming said rate-responsive pacemaker with a set of control parameters, said set of control parameters including SIR control parameters that define the manner in which said SIR signal is derived from said sensor;
said Auto-Set system comprising:
(a) means for setting said set of control parameters, including said SIR control parameters, to known initial values, said control parameters causing said rate-responsive pacemaker to assume a PASSIVE mode wherein said SIR signal is generated but does not define the rate at which stimulation pulses are generated;
(b) means for gathering diagnostic data using said rate-responsive pacemaker under known conditions, said diagnostic data including a count of said SIR signals as a function of rate during the time that said control parameters have assumed said known initial values; and
(c) means for processing the diagnostic data in order to define a multiplicity of SIR control parameters that optimally define the manner in which said SIR signal is derived from said sensor for the particular environment under which said diagnostic data was gathered.

11. The Auto-Set system, as set forth in claim 10, wherein said means for gathering diagnostic data includes means for displaying instructions to an operator of said programming device that, if followed, subject said rate-responsive pacemaker, including said sensor, to a known load.

12. The Auto-Set system, as set forth in claim 11, wherein said known load comprises a prescribed level of exercise that a patient within whom said rate-responsive pacemaker has been implanted is instructed to perform by said displaying instruction means.

13. The Auto-Set system, as set forth in claim 11, wherein the means for processing the diagnostic data includes means for manually programming at least one of the parameters included in said multiplicity of SIR control parameters into said rate-responsive pacemaker which an operator of said programming device believes are appropriate for the known load to which the pacemaker has been subjected.

14. The Auto-Set system, as set forth in claim 11, further including means for automatically programming the set of SIR control parameters defined by said retrieving and processing means into said rate-responsive pacemaker.

15. The Auto-Set system, as set forth in claim 11, wherein the SIR control parameters programmed into said pacemaker comprise a set of specified initial values, said specified initial values including a prescribed slope that relates a given sensor indicated rate (SIR) index signal to a specific SIR signal, said SIR index signal varying as a function of a physiological parameter sensed by said sensor, and wherein said means for processing said diagnostic data includes:
means for determining the highest rate range of the count of the SIR signals obtained while subjecting said rate-responsive pacemaker to said known load;
means for computing a delta rate based on the highest rate range thus determined and a programmed base rate of the pacemaker;
means for determining an SIR index signal corresponding to the delta rate thus determined and a prescribed slope, said prescribed slope being included in the SIR control parameters programmed into said rate-responsive pacemaker;

means for determining a set of SIR values corresponding to the SIR index signal thus determined and other slope values programmed into said rate-responsive pacemaker;

means for selecting one of the SIR values thus determined as a desired SIR value for the known load to which the rate-responsive pacemaker was subjected; and means for assigning a set of programmable sensor parameters that includes the slope value corresponding to said desired SIR value, said assigned set of programmable parameters comprising the multiplicity of SIR control parameters.

16. The Auto-Set system, as set forth in claim 15, wherein said means for determining the highest rate range of the count of the SIR signals obtained while subjecting said rate-responsive pacemaker to said known load includes means for determining an average rate of the highest rate range having a prescribed minimum number of counts, and wherein said means for computing said delta rate comprises means for subtracting said programmed base rate from the average rate thus determined.

17. A method for determining a proposed set of programmable sensor parameters for use within a rate-responsive pacemaker implanted within a patient comprising:

(a) setting the programmable sensor parameters within said pacemaker to a set of specified initial values, said specified initial values including a prescribed slope that relates a given sensor indicated rat (SIR) index signal to a specific SIR signal, said SIR index signal varying as a function of a sensed physiological parameter, the SIR signals accumulated over time as said SIR index signal varies comprising SIR data, said specified initial values further causing said pacemaker to assume a PASSIVE mode wherein the SIR data does not influence the operation of said rate-responsive pacemaker;

(b) instructing the patient within whom the rate-responsive pacemaker has been implanted to perform a specified task;

(c) storing said SIR data in said rate-responsive pacemaker during the time that the task specified in step (b) is being performed;

(d) estimating a desired sensor indicated rate for the rate-responsive pacemaker for the specified task performed in step (b); and (e) processing the SIR data stored in step (c) and the desired sensor indicated rate estimated in step (d) to determine a proposed set of programmable parameters for use within said rate-responsive pacemaker.

18. The method, as set forth in claim 17, further including:

(f) automatically programming said proposed set of programmable parameters into said rate-responsive pacemaker.

19. The method, as set forth in claim 17, wherein steps (c)–(e) include:

(1) determining the highest rate range of the SIR data stored in step (c) while performing the task specified in step (b);

(2) computing a delta rate based on the highest rate range determined in step (1) and a programmed base rate of the pacemaker;

(3) determining an SIR index signal corresponding to the delta rate determined in step (2) and the prescribed slope included in the programmable sensor parameters set in step (a);

(4) determining a set of SIR values corresponding to the SIR index signal determined in step (3) and other slope values programmed into said pacemaker;

(5) selecting one of the SIR values determined in step (4) as a desired SIR value for the task performed in step (b);

(6) assigning a set of programmable sensor parameters that includes the slope value corresponding to said desired SIR value, said assigned set of programmable parameters comprising the proposed set of programmable parameters.

20. The method, as set forth in claim 19, wherein step (2) comprises determining an average rate of the highest rate range determined in step (1), and subtracting said programmed base rate from said average rate to determine said delta rate.

21. The method, as set forth in claim 20, wherein step (5) includes selecting on a pre-selected preferred SIR value for the task performed in step (b).

22. The method, as set forth in claim 20, wherein step (5) includes selecting a pre-programmed preferred SIR data distribution.

* * * * *